(12) United States Patent
Tulin

(10) Patent No.: US 10,550,108 B2
(45) Date of Patent: Feb. 4, 2020

(54) POLY(ADP-RIBOSE) POLYMERASE 1 INHIBITORS STRUCTURALLY UNRELATED TO NAD

(71) Applicant: Institute for Cancer Research, Philadelphia, PA (US)

(72) Inventor: Alexei Tulin, Philadelphia, PA (US)

(73) Assignee: Institute For Cancer Research, Philadelphia, PA (US)

( * ) Notice: Subject to any disclaimer, the term of this patent is extended or adjusted under 35 U.S.C. 154(b) by 0 days.

(21) Appl. No.: 15/515,773

(22) PCT Filed: Sep. 30, 2015

(86) PCT No.: PCT/US2015/053259
§ 371 (c)(1),
(2) Date: Mar. 30, 2017

(87) PCT Pub. No.: WO2016/054237
PCT Pub. Date: Apr. 7, 2016

(65) Prior Publication Data
US 2017/0283402 A1    Oct. 5, 2017

Related U.S. Application Data

(60) Provisional application No. 62/059,201, filed on Oct. 3, 2014.

(51) Int. Cl.
| | | |
|---|---|---|
| *C07D 405/14* | (2006.01) | |
| *C07D 207/06* | (2006.01) | |
| *C07D 263/04* | (2006.01) | |
| *C07D 295/15* | (2006.01) | |
| *C07D 317/28* | (2006.01) | |
| *C07D 317/72* | (2006.01) | |
| *C07D 319/06* | (2006.01) | |
| *C07D 405/06* | (2006.01) | |

(52) U.S. Cl.
CPC ......... *C07D 405/14* (2013.01); *C07D 207/06* (2013.01); *C07D 263/04* (2013.01); *C07D 295/15* (2013.01); *C07D 317/28* (2013.01); *C07D 317/72* (2013.01); *C07D 319/06* (2013.01); *C07D 405/06* (2013.01)

(58) Field of Classification Search
CPC .......................... C07D 405/14; C07D 207/06
See application file for complete search history.

(56) References Cited

U.S. PATENT DOCUMENTS

| 3,650,749 A | 3/1972 | Willems et al. |
|---|---|---|
| 2002/0198193 A1 | 12/2002 | Barberousse et al. |
| 2009/0163545 A1 | 6/2009 | Goldfarb |
| 2009/0176765 A1 | 7/2009 | Jones et al. |
| 2009/0227590 A1 | 9/2009 | Press et al. |
| 2014/0128352 A1 | 5/2014 | Brand et al. |

FOREIGN PATENT DOCUMENTS

| CN | 102863403 | 1/2013 |
|---|---|---|
| EP | 0252482 | 1/1988 |
| WO | 2004086050 | 10/2004 |
| WO | 2008016659 | 2/2008 |
| WO | 2009131246 | 10/2009 |
| WO | 2014136086 | 9/2014 |

OTHER PUBLICATIONS

Cancer and Metastasis Reviews (1998), 17 (1), 91-106.*
Science (1999), vol. 286, 531-537.*
Cancer [online], [retrieved on Jul. 6, 2007]. Retrieved from the internet, URL; http://www.nlm.nih.gov/medlineplus/cancer.html>.*
Zhang, et al. Document No. 155:200028, retrieved from STN; Jul. 6, 2011.*
Wolinski, et al. Document No. 96:142735, retrived from STN; 1981.*
Document No. 95:132855, retrieved from STN; Jun. 13, 1981.*
Pyshchev, et al. Document No. 136:241695, retrieved from CAPLUS; May 27, 2000.*
Gavrilova, et al. Document No. 120:106824, retrieved from CAPLUS; 1993.*
Greco, et al. Document No. 116:227657, retrieved from STN; entered in STN Jun. 13, 1992.*
Goldfarb, David. Document No. 151:115083, retrieved from STN; entered in STN Jul. 23, 2009.*
PUBCHEM-CID 3260917, Sep. 6, 2005.
PUBCHEM-CID 5094348, Sep. 18, 2005.
PUBCHEM-CID 10940, Aug. 8, 2005.
PUBCHEM-CID 770075, Jul. 8, 2005.
Del Bello, et al., "Mode of interaction of 1,4-dioxane agonists at the M2 and M3 muscarinic receptor orthosteric sites", Bioorg Med Chem Lett, 2014, 24, pp. 3255-3259.
Gisvold et al., "Bascially Substituted Dioxolanes and Dioxanes", J Pharm Sciences, 1968, 57(5), pp. 784-787.
Wolinski et al., "Poszukiwanie zwiazkow antycholinergicznych VII. otrzymywanie pochodnych 2-aminoetylo-4-aminoetylo-I-2, 4-bis-(aminoetylo)-1,3-dioksolanow", Acta Poloniae Pharmaceutica, 1978, 3, pp. 265-272.
International Search Report and Written Opinion for European Application No. 15847892.5 (PCT/US2015053259) dated Apr. 10, 2018.

* cited by examiner

*Primary Examiner* — Shawquia Jackson
(74) *Attorney, Agent, or Firm* — Stradley Ronon Stevens & Young, LLP

(57) ABSTRACT

Compounds that are not related to NAD, and which target PARP1-histone H4 interaction are provided, as well as compositions of these compounds, and methods for specific inhibition of poly(ADP-ribose) polymerase 1 (PARP-1) using these compounds are provided. These PARP-1 inhibitors may be used to treat cancer in which PARP-1 activation or biologic activity plays a role, including prostate cancer, breast cancer, kidney cancer, ovarian cancer, lymphoma, leukemia, and glioblastoma, among others.

22 Claims, 7 Drawing Sheets

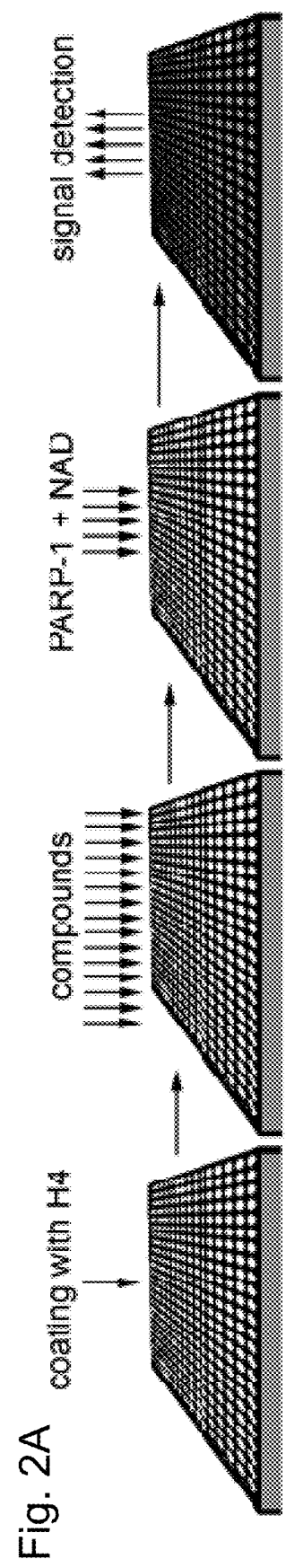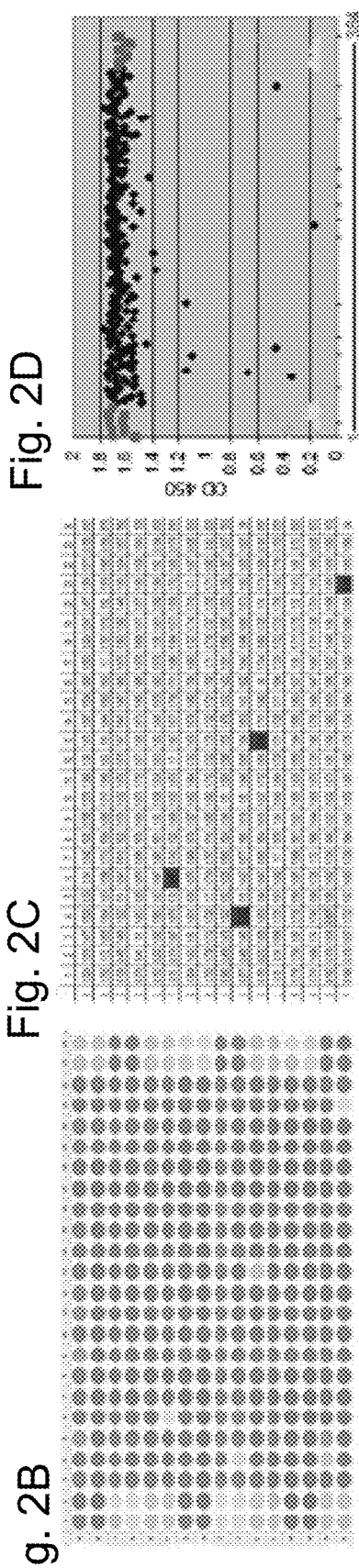
Fig. 2A   Fig. 2B   Fig. 2C   Fig. 2D

POLY(ADP-RIBOSE) POLYMERASE 1 INHIBITORS STRUCTURALLY UNRELATED TO NAD

CROSS REFERENCE TO RELATED APPLICATIONS

This application is a 35 U.S.C. § 371 national phase application of PCT Application No. PCT/US2015/053259, filed Sep. 30, 2015, which claims priority to U.S. Provisional Application No. 62/059,201, which was filed on Oct. 3, 2014, the contents of which are incorporated by reference herein, in their entirety and for all purposes.

STATEMENT OF GOVERNMENT SUPPORT

The inventions described herein were made, in part, with funds obtained from the National Institutes of Health, Grant Nos. R01 GM077452 and R01 DK082623. The U.S. government may have certain rights in these inventions.

FIELD OF THE INVENTION

The invention relates generally to the field of formulation chemistry. More particularly, the invention relates to compounds, compositions, and methods for specifically inhibiting poly(ADP)-ribose polymerase 1 (PARP1) and for treating PARP1-associated diseases including, for example, breast, kidney, prostate, and ovarian cancers, as well as lymphoma, leukemia, melanoma, and glioblastoma. The compounds are not structurally related to nicotinamide adenine dinucleotide.

BACKGROUND OF THE INVENTION

Various publications, including patents, published applications, technical articles and scholarly articles are cited throughout the specification. Each of these cited publications is incorporated by reference herein, in its entirety and for all purposes.

Poly(ADP-ribose) polymerase 1 (PARP-1) is an abundant and ubiquitous nuclear enzyme. When active, it captures nicotinamide adenine dinucleotide (NAD) to assemble long and branching molecules of Poly(ADP-ribose) (pADPr), thereby modifying itself as well as surrounding proteins. Although DNA repair is commonly accepted as its main function, recent findings indicate that PARP-1 also participates in numerous nuclear processes, including transcription regulation and epigenetic bookmarking. PARP-1 tends to localize in promoter regions of genes involved in cell adhesion and cell-to-cell signaling, controlling their expression.

PARP-1 inhibitors have been shown to selectively eliminate several types of tumorigenic cells. In recent years, PARP-1 inhibitors became popular in clinical research on novel strategies of cancer treatment and, a number of PARP-1 inhibitors are currently undergoing clinical trials for treatment of genetically disposed mutant tumors. Unfortunately, a number of clinical studies reported setbacks in research on PARP-1-based anticancer therapies.

One of the factors that may limit the potency of PARP-1 inhibitors is the majority of currently available inhibitors were designed as NAD competitors (FIGS. 1A and 1B). NAD is abundant, ubiquitous, and is used by many other enzymes. Therefore, it is very difficult to completely eliminate NAD interaction with PARP-1 without drastically affecting other metabolic processes. Moreover, as classical PARP-1 inhibitors demonstrate substantial similarities to nucleotide analogues, they obstruct functions of enzymes which utilizing nucleotides as cofactors, such as kinases.

As PARP-1 remains a viable target in cancer therapy, there remains a need for PARP-1 inhibitors that do not affect other enzymes or other normal metabolic processes. Relatedly, there remains a need for PARP-1 inhibitors that diverge from the established model of aiming at the NAD-PARP-1 interaction.

SUMMARY OF THE INVENTION

The disclosure features PARP-1 inhibitors that are believed to be independent of NAD. Compositions of such PARP-1 inhibitors are also provided, which compositions comprise the inhibitor and a carrier such as a pharmaceutically acceptable carrier, with the inhibitor preferably in an amount effective to inhibit PARP-1, preferably in a cancer cell in which PARP-1 upregulation or biologic activity play a role. The PARP-1 inhibitors may comprise a compound of the formula or pharmaceutically acceptable salt thereof:

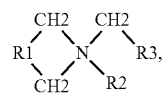

wherein:
R1 is an alkyl or ether group, a non-limiting example being —(CH$_2$)$_3$—,
R2 is either CH3 or not present, wherein when R2 is CH3, the nitrogen atom is positively charged, and
R3 is either

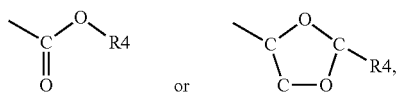

wherein R4 includes one or more ring structures.

The PARP-1 inhibitor may comprise any compound shown in Tables 1 or 2, below or a pharmaceutically acceptable salt thereof. The compound may comprise Formula I, Formula IV-1, Formula IV-2, Formula IV-3, Formula IV-4, Formula V, Formula VI, Formula VII-1, Formula VII-2, Formula VII-3, Formula VII-4, Formula VII-5, Formula VIII-1, Formula VIII-2, Formula IX-1, Formula IX-2, or a pharmaceutically acceptable salt thereof.

The PARP-1 inhibitor may comprise a compound of the formula

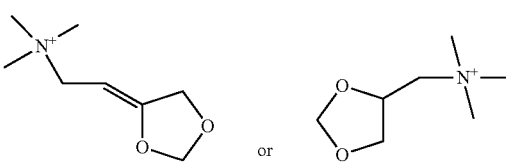

or a pharmaceutically acceptable salt thereof. The PARP-1 inhibitor may comprise any compound shown in Table 3 below or a pharmaceutically acceptable salt thereof. The compound may comprise Formula X-1 or X-2 or a pharmaceutically acceptable salt thereof.

The disclosure also features methods for inhibiting the biologic activity of PARP-1, comprising contacting PARP-1 with an amount of a compound or a pharmaceutically acceptable salt thereof effective to inhibit the biologic activity of PARP-1, the compound comprising:

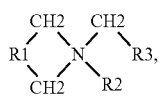

wherein:

R1 is an alkyl or ether group, a non-limiting example being —(CH$_2$)$_3$—;

R2 is either CH3 or not present, wherein when R2 is CH3, the nitrogen atom is positively charged, and R3 is either

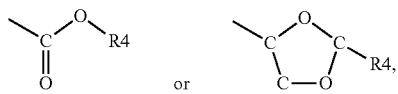

wherein R4 includes one or more ring structures.

In accordance with the methods, the compound may be present in a composition comprising a carrier. The method may be carried out in vivo, in vitro, in situ, or ex vivo. The methods may be carried out using a cell, for example, by contacting a cell with the compound or pharmaceutically acceptable salt thereof, or composition thereof. The cell may be a cancer cell. The cancer cell may be a prostate cancer cell, a breast cancer cell, a kidney cancer cell, an ovarian cancer cell, a lymphoma cell, a melanoma cell, a leukemia cell, or a glioblastoma cell. The PARP-1 inhibitor may comprise any compound shown in Tables 1 or 2 below. The compound may comprise Formula I, Formula IV-1, Formula IV-2, Formula IV-3, Formula IV-4, Formula V, Formula VI, Formula VII-1, Formula VII-2, Formula VII-3, Formula VII-4, Formula VII-5, Formula VIII-1, Formula VIII-2, Formula IX-1, Formula IX-2, or a pharmaceutically acceptable salt thereof.

The disclosure also features methods for inhibiting the biologic activity of PARP-1, comprising contacting PARP-1 with an amount of a compound or a pharmaceutically acceptable salt thereof effective to inhibit the biologic activity of PARP-1, the compound comprising:

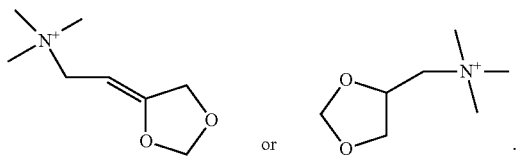

In accordance with the methods, the compound may be present in a composition comprising a carrier. The method may be carried out in vivo, in vitro, in situ, or ex vivo. The methods may be carried out using a cell, for example, by contacting a cell with the compound or pharmaceutically acceptable salt thereof, or composition thereof. The cell may be a cancer cell. The cancer cell may be a prostate cancer cell, a breast cancer cell, a kidney cancer cell, an ovarian cancer cell, a lymphoma cell, a melanoma cell, a leukemia cell, or a glioblastoma cell. The PARP-1 inhibitor may comprise any compound shown in Table 3 below or a pharmaceutically acceptable salt thereof. The compound may comprise Formula X-1 or X-2 or a pharmaceutically acceptable salt thereof.

Cancer treatment methods are also provided. The methods may comprise administering to a cancer patient in need thereof a treatment-effective amount of a PARP-1 inhibitor compound or pharmaceutically acceptable salt thereof, or composition thereof, the PARP-1 inhibitor compound comprising:

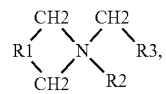

wherein:

R1 is an alkyl or ether group, a non-limiting example being —(CH$_2$)$_3$—;

R2 is either CH3 or not present, wherein when R2 is CH3, the nitrogen atom is positively charged, and R3 is either

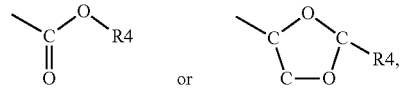

wherein R4 includes one or more ring structures.

The PARP-1 inhibitor may comprise any compound shown in Tables 1 or 2, below or a pharmaceutically acceptable salt thereof. The compound may comprise Formula I, Formula IV-1, Formula IV-2, Formula IV-3, Formula IV-4, Formula V, Formula VI, Formula VII-1, Formula VII-2, Formula VII-3, Formula VII-4, Formula VII-5, Formula VIII-1, Formula VIII-2, Formula IX-1, Formula IX-2, or a pharmaceutically acceptable salt thereof. Use of such compounds, salts, and compositions in the treatment of cancer are further provided. The cancer patient may be a prostate cancer patient and the cancer may comprise prostate cancer, the cancer patient may be a breast cancer patient and the cancer may comprise breast cancer, the cancer patient may be a kidney cancer patient and the cancer may comprise kidney cancer, the cancer patient may be an ovarian cancer patient and the cancer may comprise ovarian cancer, the cancer patient may be a glioblastoma patient and the cancer may comprise glioblastoma, the cancer patient may be a melanoma patient and the cancer may comprise melanoma, the cancer patient may be a lymphoma patient and the cancer may comprise lymphoma, or cancer patient may be a leukemia patient and the cancer may comprise leukemia.

The methods may comprise administering to a cancer patient in need thereof a treatment-effective amount of a PARP-1 inhibitor compound or pharmaceutically acceptable salt thereof, or composition thereof, the PARP-1 inhibitor compound comprising:

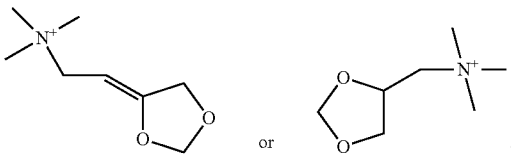

The PARP-1 inhibitor may comprise any compound shown in Table 3 below or a pharmaceutically acceptable salt thereof. The compound may comprise Formula X-1 or X-2 or a pharmaceutically acceptable salt thereof. Use of such compounds, salts, and compositions in the treatment of cancer are further provided. The cancer patient may be a prostate cancer patient and the cancer may comprise prostate cancer, the cancer patient may be a breast cancer patient and the cancer may comprise breast cancer, the cancer patient may be a kidney cancer patient and the cancer may comprise kidney cancer, the cancer patient may be an ovarian cancer patient and the cancer may comprise ovarian cancer, the cancer patient may be a glioblastoma patient and the cancer may comprise glioblastoma, the cancer patient may be a melanoma patient and the cancer may comprise melanoma, the cancer patient may be a lymphoma patient and the cancer may comprise lymphoma, or cancer patient may be a leukemia patient and the cancer may comprise leukemia.

BRIEF DESCRIPTION OF THE DRAWINGS

FIG. 1A shows PARP-1 binds NAD+ by NAD-binding pocket organized by three amino acids, Gly-863, Ser-904 and Tyr-907 interacting mostly with nicotinamide part of NAD. FIG. 1B shows most of current PARP-1 inhibitors are developed from nicotinamide pharmacophore. FIG. 1C shows three ways of PARP-1 regulation: 1) competition with NAD for binding, 2) disruption of PARP-1 interaction with histones and 3) obstruction of binding with DNA. Arrowhead shows site of PARP-1 digestion by Caspase 3, which cleaves off DNA binding Zn-fingers of PARP-1, thus, abolishing DNA-dependent PARP-1 activation. FIG. 1D. shows interaction with the purified core histone H4 activates PARP1 in a DNA-independent manner. Full-length PARP-1 protein (left) and PARP1 protein cleaved by Caspase 3 (right) were pre-incubated with randomly broken DNA or core histone H4, followed by mixing with NAD. The products of PARP-1 enzymatic activity, poly(ADP-ribose), were detected after PAGE on a Western blot using the anti-pADPr antibody. These data clearly demonstrate that the DNA-binding domain of PARP1 (Zn-fingers I and II) is not required for histone-dependent PARP1 activation. FIG. 1E shows a schematic representation of the pipeline used for identifying PARP-1 inhibitors. FIG. 1F-G show data were visualized in a color-coded table representing 384-well plate, in which potential inhibitors could be identified as green or yellow circles corresponding to wells that had minimal pADPr signal (F) or on a graph representing this signal relatively positive (yellow) or negative (pink) when compared to controls (G).

FIGS. 2A through 2E illustrate a new screening strategy for the identification of PARP-1 inhibitors. FIG. 2A shows a schematic representation of the pipeline used for identifying PARP-1 inhibitors. FIGS. 2B-D show data visualized in a color-coded table representing 384-well plate, in which potential inhibitors could be identified as green or yellow circles corresponding to wells that had minimal pADPr signal (B) or as a table with number reflecting actual ELISA signal (C) or on a graph representing this signal relatively positive (yellow) or negative (pink) when compared to controls (D). FIG. 2E shows sorting new PARP-1 inhibitors based on presence of an obvious structural core, similar to known biologically active molecules. 14 subgroups were identified. Structural cores and numbers of molecules falling in each group are indicated.

FIG. 3A shows the molecular structures of new PARP-1 inhibitors. FIG. 3B shows a comparative analysis of PARP-1 activity in BT474, PC-3, and RCC cells cultured without and with classical PARP-1 inhibitors, 4ANI or PJ34, and new inhibitors identified in our screen. To detect pADPr on Western blot, we used mAb 10H antibody against pADPr. pAb antibody against Actin was used as a loading control. Reduction of pADPr was detected by a Western blot for inhibitor-treated cells relative to DMSO-treated cells. FIG. 3C shows new PARP-1 inhibitors suppress malignancy potential of PC-3 cells. Clonogenic cell survival assays. PC-3 cells were plated into 24-well plates. Cells were allowed to adhere overnight and were treated with one of non-NAD-like inhibitor (5F02, 4D11, 5A03, 5H03, 1C09), Olaparib, and both for 14 days. Colonies were counted and plotted on the graph. Data were fitted to exponential and logarithmic decay models using nonlinear curve fitting module of Statistica 7.0 software. The best fitting models for each inhibitor are represented on the chart. FIG. 3D shows new PARP-1 inhibitors show synergistic interaction with Olaparib. Data were fitted to exponential and logarithmic decay models using nonlinear curve fitting module of Statistica 7.0 software. The best fitting models for each inhibitor are represented on the chart. E-F. Non-NAD-like PARP-1 inhibitors suppress tumor growth in vivo. 5F02 inhibitor suppresses growth of androgen-independent PC-3 (FIG. 3E) and renal cell carcinoma (PNX) (FIG. 3F) xenograft tumors in vivo. Ectopic PC-3 or RCC xenograft tumors were established in 6-week-old male C.B17/Icr-scid mice. Animals were treated intraperitoneally with non-NAD-like inhibitor 5F02 (23 mg/kg), classical PARP-1 inhibitor Olaparib (Olap) (50 mg/kg) or vehicle (PBS) 5 days a week. Values shown represent means (n=5)+SEM. C-F. Data were fitted to exponential growth models using nonlinear curve fitting module of Statistica 7.0 software. Error bars correspond to standard deviation based on 5 repeats.

FIG. 6C illustrates 5F02 inhibitor suppresses pADP-ribosylation in androgen-independent PC-3 or RCC xenograft tumors in vivo. pADPr was detected on Western-blots.

DETAILED DESCRIPTION OF THE INVENTION

Various terms relating to aspects of the invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

Subject and patient are used interchangeably. A subject may be any animal, including mammals such as companion animals, laboratory animals, and non-human primates. Human beings are preferred.

Inhibiting comprises reducing, decreasing, blocking, preventing, delaying, inactivating, desensitizing, stopping, and/or downregulating the biologic activity or expression of a molecule or pathway of interest.

Figure 1A:
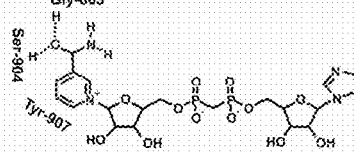
FIGS. 1A through 1G shows the design of a screening strategy for the identification of PARP-1 inhibitors.
Figure 1C:
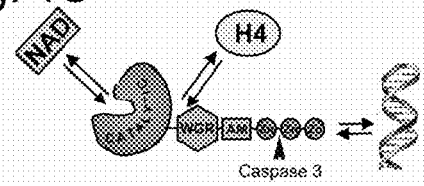
Figure 1B:
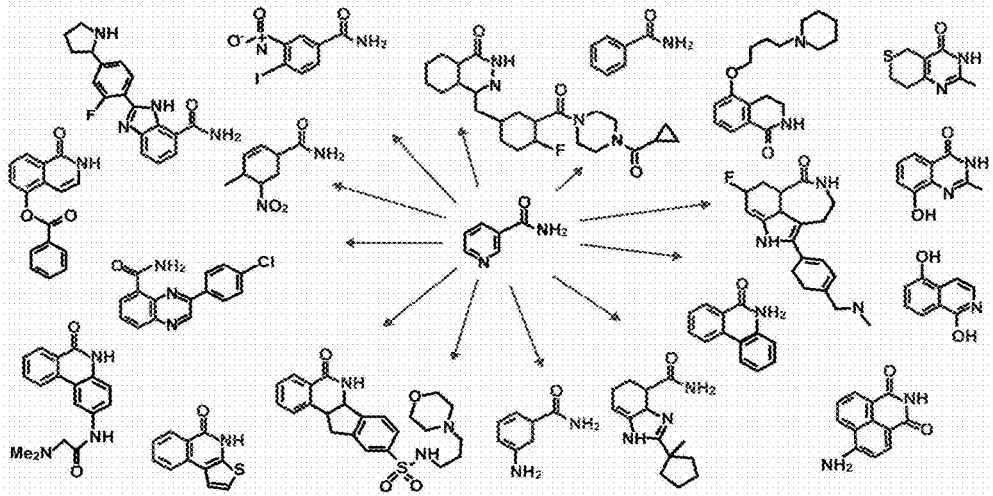
Figure 1D:
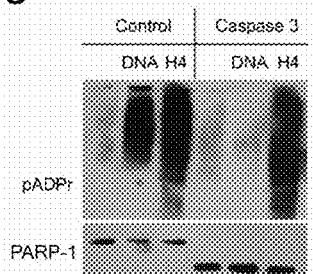

To overcome the limitation of NAD-like PARP-1 inhibitors, molecules that inhibit PARP-1, yet are structurally unrelated to NAD were screened and identified. A blind screen of a random small molecule collection containing 50,000 compounds was used. PARP-1 can be regulated by competing for binding with NAD, as well as by two additional routes: obstruction of PARP-1 binding with DNA and disruption of PARP-1 interaction with histone H4. Instead of targeting NAD binding to PARP-1, molecules that disrupt PARP-1 activation by the core histone H4 (FIG. 1C) were screened. The H4-dependent PARP-1 activation is stronger and more prolonged than the DNA-dependent (FIG. 1D). Besides identifying NAD competitors, the screen identified molecules that show no similarity to NAD, other nucleotides, or to any known PARP-1 inhibitor. Further testing of a subset of these compounds demonstrated their efficacy toward inhibiting PARP-1 in cancer cells as well as their ability to suppress the tumorigenic capacity of prostate and kidney cancer with greater efficacy than clinically approved drugs and the NAD-competitor Olaparib.

It has been observed in accordance with the invention that certain compounds that are not structural analogs or otherwise structurally similar or related to NAD can inhibit the biologic activity of poly(ADP-ribose) polymerase 1 (PARP1) without substantially inhibiting the biologic activity of other proteins and pathways that utilize NAD. These inhibitors reduce the negative effects on healthy cells that are induced by traditional, NAD-like PARP1 inhibitors and, thus, may be used to selectively kill cancer cells by exhibiting their inhibitory effect on PARP1-expressing cancer cells. Selective inhibition of PARP1 has implications for treatment of certain types of cancers and other diseases, disorders, or conditions that are caused by, facilitated by, exacerbated by, or otherwise involve biochemical pathways modulated or regulated by the biologic activity PARP1. Accordingly, the invention features compounds, compositions, and methods for inhibiting the biologic activity of PARP1, as well as methods for treating cancers in which PARP1 is expressed. The methods may be carried out in vitro, ex vivo, in vivo, or in situ.

It is believed that the PARP1 pathway is directly involved in the malignant transformation of healthy cells. It is further believed that PARP1 plays a role in tumorigenesis, and the progression from a pre-malignancy to a malignant state. Thus, PARP1 inhibition may, in turn, inhibit transformation of a healthy cell to a premalignant cell. PARP1 inhibition may also, in turn, inhibit transformation of a premalignant cell to a malignant cell. PARP1 inhibition preferably is independent of NAD and, more preferably, relates to PARP1 interaction with histone H4.

Previous iterations of PARP1 inhibitors stemmed from the role PARP1 is believed to play in DNA repair. PARP1 is a NAD-dependent enzyme whose activity can be regulated by competing for binding with NAD. Accordingly, such inhibitors have been designed as NAD mimetics. Examples of such NAD mimetics include 3AB (Formula A), 4-ANI (Formula B), PJ34 (Formula C), and Olaparib (Formula D). To overcome limitation of NAD-like PARP-1 inhibitors, compounds structurally unrelated to NAD were evaluated. PARP1 can be regulated by competing for binding with NAD, by obstruction of PARP1 binding with DNA, or by disruption of PARP1 interaction with histone H4 (FIG. 1B). Thus, the evaluation of new inhibitors considered molecules that target PARP1 interaction with histones, via a new assay and a blind screen of 50,000 small molecule compounds. This screen identified NAD competitors as well as molecules that disrupt PARP1 interaction with H4 or block the transduction of conformational changes within PARP1 molecule. In accordance with this disclosure, PARP1 inhibition preferably is independent of NAD and, more preferably, relates to PARP1 interaction with histone H4. 3AB:

(Formula A)

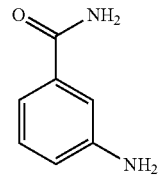

(Formula B)

4-ANI

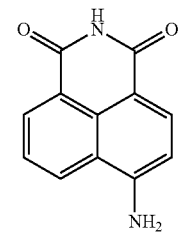

(Formula C)

PJ34

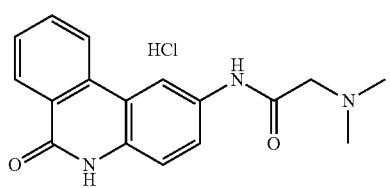

-continued (Formula D)

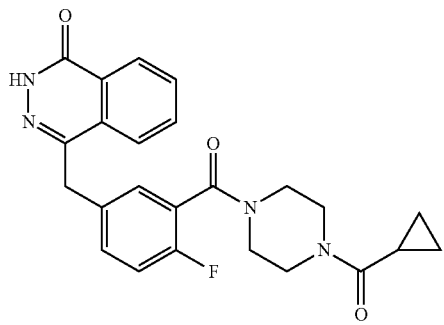

Olaparib

The screening platform included a PARP1 activation assay in plates coated with histone H4. PARP1 reactions were set up in each well of the plate in the presence of a single small molecule test compound or a positive or negative control compound. The product of the reaction between PARP1 and H4, poly-ADP-ribose, was then quantified, with absorbance at 650 nm or 450 nm used as an indicator of PARP1 activity (FIG. 2A). The screen identified 903 small molecule inhibitors from the population of test compounds. Further analysis eliminated negligible structural differences, trimming the pool of selected compounds to 639. 373 of these small molecules were found to inhibit PARP1 at the same level or at an enhanced level relative to 4-ANI and PJ34. Additional analysis removed identified inhibitors that have minimal structural similarity to known PARP1 inhibitors, identifying a group of 17 small molecules with no significant structural similarity to known PARP1 inhibitors or to NAD.

15 of the 17 identified compounds shared a common backbone of formula I:

(Formula I)

$$R1\diagdown_{CH_2}^{CH_2}\diagup N\diagdown_{R2}^{CH_2}\diagup R3$$

where R1 is an alkyl or ether group, R2 is either CH3 or not present, and R3 is either formula II or Formula III, where R4 includes one or more ring structures. When R2 is —CH3, the nitrogen atom is positively charged. Particularly in the 15 of the 17 identified compounds, R1 is —(CH2)2-, —(CH2)3-, or —(CH2)O(CH2)-.

(Formula II)

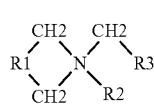

(Formula III)

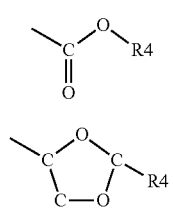

Among the 17 molecules identified by the screening platform, it was determined that structurally, these molecules could be split into 3 groups: (1) where R3 is Formula II; where R3 is Formula III; and (3) two molecules showing similarity to Group (2) in that they also possess dioxolane-4-yl in their structure, but are structurally distinct in other respects.

Among the first group where R3 is Formula II, the molecules contain a core element of 2-(N-methylpiperidin-1-yl)acetate (i.e., R1=—(CH2)3-; Formulas IV-1, IV-2, IV-3, IV-4 in Table 1), 2-(N-methylmorpholino)acetate (i.e., R1=—(CH2)O(CH2)-; Formula V in Table 1) or 2-(N-methylpyrrolidine-1-yl)acetate (i.e., R1=—(CH2)2-; Formula VI in Table 1).

TABLE 1

| Formula | R1 | Structure |
|---|---|---|
| IV-1 | —(CH2)3— | 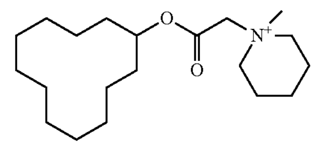 [SMILES: C[N+]1(CC(=O)OC2CCCCCCCCCCC2)CCCCC1] |
| IV-2 | —(CH2)3— | 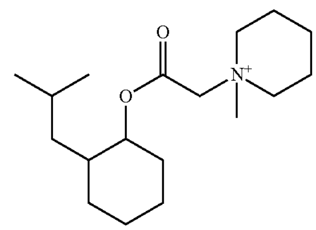 [SMILES: CC(C)CC1CCCCC1OC(=O)C[N+]1(C)CCCCC1] |
| IV-3 | —(CH2)3— | 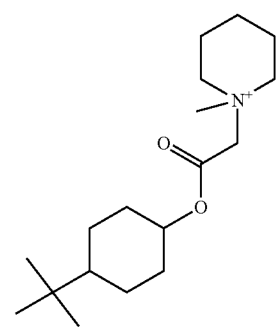 [SMILES: CC(C)(C)C1CCC(OC(=O)C[N+]2(C)CCCCC2)CC1] |
| IV-4 | —(CH2)3— | 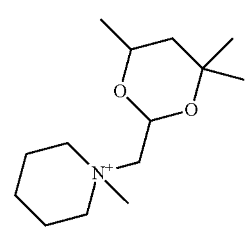 [SMILES: CC1CC(C)(C)OC(C[N+]2(C)CCCCC2)O1] |
| V | —(CH2)O(CH2)— | 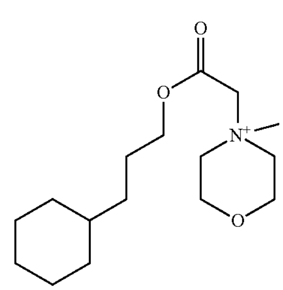 [SMILES: C[N+]1(CC(=O)OCCCC2CCCCC2)CCOCC1] |

TABLE 1-continued

| Formula | R1 | Structure |
|---|---|---|
| VI | —(CH2)2— | 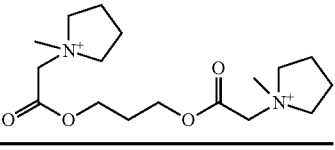 |

Among the second subgroup where R3 is Formula III, the molecules contain a core element of 1-((1,3-dioxolane-4-yl)methyl)piperidine (R1=—(CH2)3-; Formulas J, K, L, M, and N in Table 2), 1-((1,3-dioxolane-4-yl)methyl)N-methylmorpholine (R1=—(CH2)O(CH2)-; Formulas 0 and P in Table 2) or 1-((1,3-dioxolane-4-yl)methyl)N-methylpyrrolidine (R1=—(CH2)2-; Formula Q and R in Table 2).

TABLE 2

| Formula | R1 | Structure |
|---|---|---|
| VII-1 | —(CH2)3— | 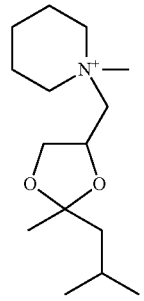 [SMILES: CC(C)CC1(C)OCC(C[N+]2(C)CCCCC2)O1] |
| VII-2 | —(CH2)3— | 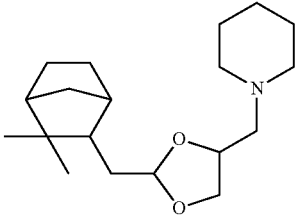 [SMILES: CC1(C)C2CCC(C2)C1CC1OCC(CN2CCCCC2)O1] |
| VII-3 | —(CH2)3— | 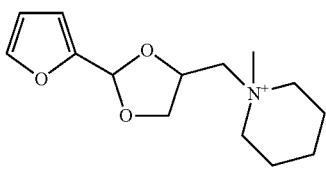 [SMILES: C[N+]1(CC2COC(c3ccco3)O2)CCCCC1] |
| VII-4 | —(CH2)3— | 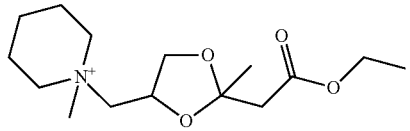 [SMILES: CCOC(=O)CC1(C)OCC(C[N+]2(C)CCCCC2)O1] |
| VII-5 | —(CH2)3— | 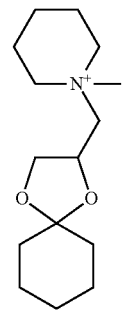 [SMILES: C[N+]1(CC2COC3(CCCCC3)O2)CCCCC1] |

TABLE 2-continued

| Formula | R1 | Structure |
|---|---|---|
| VIII-1 | —(CH2)O(CH2)— | 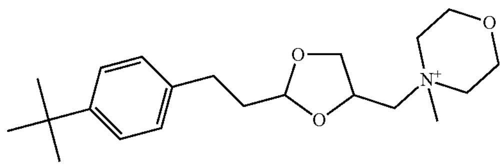 [SMILES: CC(C)(C)c1ccc(CCC2OCC(C[N+]3(C)CCOCC3)O2)cc1] |
| VIII-2 | —(CH2)O(CH2)— | 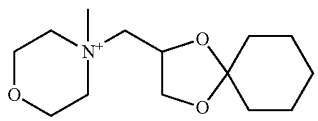 [SMILES: C[N+]1(CC2COC3(CCCCC3)O2)CCOCC1] |
| IX-1 | —(CH2)2— | 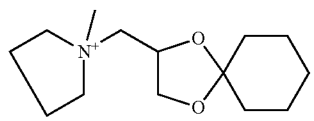 [SMILES: C[N+]1(CC2COC3(CCCCC3)O2)CCCC1] |
| IX-2 | —(CH2)2— | 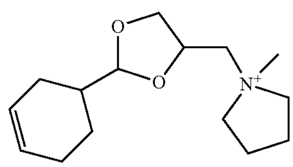 [SMILES: C[N+]1(CC2COC(C3CC=CCC3)O2)CCCC1] |

The third subgroup of compounds includes Formula S and Formula T (Table 3), which are structurally similar to the compounds of the second subgroup in that they also possess dioxolane-4-yl in their structure.

TABLE 3

| Formula | Compound |
|---|---|
| X-1 | |
| X-2 | |

Pharmaceutically acceptable salts may be acid or base salts. Non-limiting examples of pharmaceutically acceptable salts include sulfates, methosulfates, methanesulfates, pyrosulfates, bisulfates, sulfites, bisulfites, nitrates, besylates, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, dioates, benzoates, chlorobenzoates, methylbenzoates, dinitromenzoates, hydroxybenzoates, methoxybenzoates, phthalates, sulfonates, toluenesulfonates, xylenesulfonates, pheylacetates, phenylpropionates, phenylbutyrates, citrates, lactates, γ-hydroxybutyrates, glycollates, tartrates, methanesulfonates, propanesulfonates, mandelates, and other salts customarily used or otherwise FDA-approved.

The compounds may be formulated as a composition, for example, with a carrier. Compositions may comprise a compound of Formula I, Formula IV-1, Formula IV-2, Formula IV-3, Formula IV-4, Formula V, Formula VI, Formula VII-1, Formula VII-2, Formula VII-3, Formula VII-4, Formula VII-5, Formula VIII-1, Formula VIII-2, Formula IX-1, Formula IX-2, Formula X-1, Formula X-2 or a pharmaceutically acceptable salt thereof. The composition may include more than one, including any combination, of Formula I, Formula IV-1, Formula IV-2, Formula IV-3, Formula IV-4, Formula V, Formula VI, Formula VII-1, Formula VII-2, Formula VII-3, Formula VII-4, Formula VII-5, Formula VIII-1, Formula VIII-2, Formula IX-1, Formula IX-2, Formula X-1, and Formula X-2. The composition may include other PARP1 inhibitors (e.g., Formula A, Formula B, Formula C, Formula D, or combinations thereof). The carrier is preferably a pharmaceutically acceptable carrier. Pharmaceutically acceptable carriers include aqueous vehicles such as water, alcohol (e.g., ethanol or glycol), saline solutions, dextrose solutions, and balanced salt solutions, as well as nonaqueous vehicles such as alcohols and oils, including plant or vegetable-derived oils such as olive oil, cottonseed oil, corn oil, canola oil, sesame oil, and other non-toxic oils. The compositions may comprise one or more pharmaceutically acceptable excipients.

The compositions preferably comprise an effective amount of the compound such as a compound having Formula I, Formula IV-1, Formula IV-2, Formula IV-3, Formula IV-4, Formula V, Formula VI, Formula VII-1, Formula VII-2, Formula VII-3, Formula VII-4, Formula VII-5, Formula VIII-1, Formula VIII-2, Formula IX-1, Formula IX-2, Formula X-1, Formula X-2, or any combination thereof, or pharmaceutically acceptable salt of any of Formula I, Formula IV-1, Formula IV-2, Formula IV-3, Formula IV-4, Formula V, Formula VI, Formula VII-1, Formula VII-2, Formula VII-3, Formula VII-4, Formula VII-5, Formula VIII-1, Formula VIII-2, Formula IX-1, Formula IX-2, Formula X-1, Formula X-2, or any combination thereof.

The compositions may be prepared to provide from about 0.05 mg to about 500 mg of the compound, or pharmaceutically acceptable salt thereof. The compositions may comprise from about 1 mg to about 200 mg of the compound, may comprise from about 10 mg to about 200 mg of the compound, may comprise from about 10 mg to about 100 mg of the compound, may comprise from about 50 mg to about 100 mg of the compound, may comprise from about 20 mg to about 400 mg of the compound, may comprise from about 100 mg to about 300 mg of the compound, and may comprise from about 50 mg to about 250 mg of the compound, or pharmaceutically acceptable salt thereof.

The compositions may be formulated for administration to a subject in any suitable dosage form. The compositions may be formulated for oral, buccal, nasal, transdermal, parenteral, injectable, intravenous, subcutaneous, intramuscular, rectal, or vaginal administrations. The compositions may be formulated in a suitable controlled-release vehicle, with an adjuvant, or as a depot formulation.

Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions.

Solid dosage forms include tablets, pills, powders, bulk powders, capsules, granules, and combinations thereof. Solid dosage forms may be prepared as compressed, chewable lozenges and tablets which may be enteric-coated, sugar coated or film-coated. Solid dosage forms may be hard or encased in soft gelatin, and granules and powders may be provided in non-effervescent or effervescent form. Solid dosage forms may be prepared for dissolution or suspension in a liquid or semi-liquid vehicle prior to administration. Solid dosage forms may be prepared for immediate release, controlled release, or any combination thereof. Controlled release includes, but is not limited to delayed release, sustained release, timed pulsatile release, and location-specific pulsatile release, and combinations thereof.

Liquid dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions may be oil-in water or water-in-oil emulsions.

Pharmaceutically acceptable excipients utilized in solid dosage forms include coatings, binders, lubricants, diluents, disintegrating agents, coloring agents, flavoring agents, preservatives, sweeteners, and wetting agents. Enteric-coated tablets, due to their enteric-coating, resist the action of stomach acid and dissolve or disintegrate in the neutral or alkaline intestines. Other examples of coatings include sugar coatings and polymer coatings. Sweetening agents are especially useful in the formation of chewable tablets and lozenges. Pharmaceutically acceptable excipients used in liquid dosage forms includes solvents, suspending agents, dispersing agents, emulsifying agents, surfactants, emollients, coloring agents, flavoring agents, preservatives, and sweeteners.

Non-limiting examples of binders include glucose solution, acacia mucilage, gelatin solution, sucrose and starch paste. Non-limiting examples of lubricants include talc, starch, magnesium or calcium stearate, lycopodium and stearic acid. Non-limiting examples of diluents include lactose, sucrose, starch, kaolin, salt, mannitol and dicalcium phosphate. Non-limiting examples of disintegrating agents include corn starch, potato starch, bentonite, methylcellulose, agar and carboxymethylcellulose. Non-limiting examples of emulsifying agents include gelatin, acacia, tragacanth, bentonite, and surfactants such as polyoxyethylene sorbitan monooleate. Non-limiting examples of suspending agents include sodium carboxymethylcellulose, pectin, tragacanth, veegum and acacia.

Non-limiting examples of coloring agents include any of the approved certified water soluble FD and C dyes, mixtures thereof, and water insoluble FD and D dyes suspended on alumina hydrate. Non-limiting examples of sweetening agents include dextrose, sucrose, fructose, lactose, mannitol and artificial sweetening agents such as saccharin, aspartame, sucralose, acelsulfame potassium, and other artificial sweeteners. Non-limiting examples of flavoring agents include synthetic flavors and natural flavors extracted from plants such as fruits and mints, and synthetic blends of compounds which produce a pleasant sensation. Non-limiting examples of wetting agents include propylene glycol monostearate, sorbitan monooleate, diethylene glycol monolaurate and polyoxyethylene laural ether. Non-limiting examples of enteric-coatings include fatty acids, fats, waxes, shellac, ammoniated shellac and cellulose acetate phthalates. Non-limiting examples of film coatings include hydroxyethylcellulose, sodium carboxymethylcellulose, polyethylene glycol 4000 and cellulose acetate phthalate. Non-limiting examples of preservatives include glycerin, methyl and propylparaben, ethylparaben, butylparaben, isobutylparaben, isopropylparaben, benzylparaben, citrate, benzoic acid, sodium benzoate and alcohol.

Elixirs include clear, sweetened, hydroalcoholic preparations. Pharmaceutically acceptable carriers used in elixirs include solvents. Syrups include concentrated aqueous solutions of a sugar, for example, sucrose, and may contain a preservative. An emulsion is a two-phase system in which one liquid is dispersed throughout another liquid. Pharmaceutically acceptable carriers used in emulsions may include emulsifying agents and preservatives. Suspensions may use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substance used in effervescent granules, to be reconstituted into a liquid oral dosage form, include organic acids and a source of carbon dioxide. Sources of carbon dioxide include sodium bicarbonate and sodium carbonate. Coloring and flavoring agents may be used in all such dosage forms.

Additional excipients that may be included in any dosage forms include, but are not limited to antimicrobial agents, isotonic agents, buffers, antioxidants, local anesthetic agents, sequestering or chelating agents, analgesic agents, antiemetic agents, and other agents to enhance selected characteristics of the formulation.

Antimicrobial agents may be cidal or static, and may be antimicrobial, antifungal, antiparasitic, or antiviral. Non-limiting examples of commonly used antimicrobial agents include phenols or cresols, mercurials, benzyl alcohol, chlorobutanol, methyl and propyl p-hydroxybenzoic acid esters, thimerosal, benzalkonium chloride and benzethonium chloride. Acidic or basic pH may be used for antimicrobial effects in some aspects. Non-limiting examples of isotonic agents include sodium chloride and dextrose. Non-limiting examples of buffers include phosphate and citrate buffers. A non-limiting example of a chelating agent for metal ions is EDTA.

The disclosure also features methods for inhibiting PARP1. In accordance with methods including PARP 1 inhibition, the PARP1 inhibition preferably is independent of NAD and, more preferably, relates to PARP1 interaction with histone H4. Such methods may comprise treatment methods, by which PARP1 inhibition treats any condition in which PARP1 expression and/or activation and/or biologic activity plays a role, including cancer.

In some aspects, the methods comprise contacting PARP1 with an effective amount of a compound or composition comprising Formula I, Formula II, Formula III, Formula IV, Formula V, Formula VI, Formula VI, or Formula VIII, or any combination thereof or any pharmaceutically acceptable salt thereof. The composition may comprise any dosage form and/or any excipients, including those described or exemplified herein.

The biologic activity of PARP is inhibited by the compound or composition with less than about a 100 nM $IC_{50}$, more with less than about a 50 nM $IC_{50}$, more preferably with less than about a 40 nM $IC_{50}$, more preferably with less than about a 30 nM $IC_{50}$, more preferably with less than about a 20 nM $IC_{50}$, more preferably with less than about a 10 nM $IC_{50}$, more preferably with less than about a 8 nM $IC_{50}$, and more preferably with less than about a 5 nM $IC_{50}$.

In some aspects, the methods comprise contacting a cell expressing PARP1 with an effective amount of a compound or composition comprising Formula I, Formula IV-1, Formula IV-2, Formula IV-3, Formula IV-4, Formula V, Formula VI, Formula VII-1, Formula VII-2, Formula VII-3, Formula VII-4, Formula VII-5, Formula VIII-1, Formula VIII-2, Formula IX-1, Formula IX-2, Formula X-1, Formula X-2, or any combination thereof or any pharmaceutically acceptable salt thereof. The composition may comprise any dosage form and/or any excipients, including those described or exemplified herein. In contacting the cell in this way, the compound or composition inhibits the biologic activity of PARP1 in the cell, preferably in a NAD-independent manner, and preferably by disrupting PARP1 interaction with histone H4. The cell may be any cell in which PARP1 is expressed or is active. The cell may be a cell stably transformed with a nucleic acid encoding PARP. The cell may be a cell line. The cell may be within the body of a subject. The cell may be a cancer cell such as a prostate cancer cell, a breast cancer cell, a kidney cancer cell, an ovarian cancer cell, a lymphoma cell, a melanoma cell, a leukemia cell, or a glioblastoma cell. The cell may be any cancer cell in which PARP1 is expressed or is active or is otherwise sensitive to treatment with a PARP1 inhibitor described or exemplified herein.

In some aspects, a method for treating a cancer patient comprises administering to the patient a compound or composition comprising Formula I, Formula IV-1, Formula IV-2, Formula IV-3, Formula IV-4, Formula V, Formula VI, Formula VII-1, Formula VII-2, Formula VII-3, Formula VII-4, Formula VII-5, Formula VIII-1, Formula VIII-2, Formula IX-1, Formula IX-2, Formula X-1, Formula X-2, or any combination thereof or any pharmaceutically acceptable salt thereof, in an amount effective to treat the cancer. The effective amount is preferably an amount effective to inhibit the biologic activity of PARP1 in cancer cells within the patient's body. PARP1 inhibition in the body kills the cancer cells in which PARP1 is expressed and is active, thereby treating the cancer in the patient. The patient is preferably a human cancer patient. The cancer may be any cancer in which PARP1 is expressed and is active, including without limitation prostate cancer, breast cancer, kidney cancer, ovarian cancer, lymphoma, leukemia, melanoma, or glioblastoma.

Administration may be according to any technique or route suitable to the cancer being treated or the patient's needs. Administration may be, for example, oral, parenteral, or via direct injection. Administration may be directly to the tumor or to a location proximal to the tumor. Delivery may be via the bloodstream. Delivery may include active targeting, for example, by conjugating the compound to an antibody that binds to an antigen on the tumor being treated. Delivery may be passive.

Use of a PARP-1 inhibitor according to Formula I, Formula IV-1, Formula IV-2, Formula IV-3, Formula IV-4, Formula V, Formula VI, Formula VII-1, Formula VII-2, Formula VII-3, Formula VII-4, Formula VII-5, Formula VIII-1, Formula VIII-2, Formula IX-1, Formula IX-2, Formula X-1, Formula X-2, or a pharmaceutically acceptable salt thereof, or a composition thereof in the treatment of cancer or tumors are provided. The disclosure features use of a PARP-1 inhibitor according to Formula I, Formula IV-1, Formula IV-2, Formula IV-3, Formula IV-4, Formula V, Formula VI, Formula VII-1, Formula VII-2, Formula VII-3, Formula VII-4, Formula VII-5, Formula VIII-1, Formula VIII-2, Formula IX-1, Formula IX-2, Formula X-1, Formula X-2, or a pharmaceutically acceptable salt thereof, or a composition thereof in the treatment of prostate cancer. The disclosure features use of a PARP-1 inhibitor according to Formula I, Formula IV-1, Formula IV-2, Formula IV-3, Formula IV-4, Formula V, Formula VI, Formula VII-1, Formula VII-2, Formula VII-3, Formula VII-4, Formula VII-5, Formula VIII-1, Formula VIII-2, Formula IX-1, Formula IX-2, Formula X-1, Formula X-2, or a pharmaceutically acceptable salt thereof, or a composition thereof in the treatment of kidney cancer. The disclosure features use of a PARP-1 inhibitor according to Formula I, Formula IV-1, Formula IV-2, Formula IV-3, Formula IV-4, Formula V, Formula VI, Formula VII-1, Formula VII-2, Formula VII-3, Formula VII-4, Formula VII-5, Formula VIII-1, Formula VIII-2, Formula IX-1, Formula IX-2, Formula X-1, Formula X-2, or a pharmaceutically acceptable salt thereof, or a composition thereof in the treatment of breast cancer. The disclosure features use of a PARP-1 inhibitor according to Formula I, Formula IV-1, Formula IV-2, Formula IV-3, Formula IV-4, Formula V, Formula VI, Formula VII-1, Formula VII-2, Formula VII-3, Formula VII-4, Formula VII-5, Formula VIII-1, Formula VIII-2, Formula IX-1, Formula IX-2, Formula X-1, Formula X-2, or a pharmaceutically acceptable salt thereof, or a composition thereof in the treatment of ovarian cancer. The disclosure features use of a PARP-1 inhibitor according to Formula I, Formula IV-1, Formula IV-2, Formula IV-3, Formula IV-4, Formula V, Formula VI, Formula VII-1, Formula VII-2, Formula VII-3, Formula VII-4, Formula VII-5, Formula VIII-1, Formula VIII-2, Formula IX-1, Formula IX-2, Formula X-1, Formula X-2, or a pharmaceutically acceptable salt thereof, or a composition thereof in the treatment of melanoma. The disclosure features use of a PARP-1 inhibitor according to Formula I, Formula IV-1, Formula IV-2, Formula IV-3, Formula IV-4, Formula V, Formula VI, Formula VII-1, Formula VII-2, Formula VII-3, Formula VII-4, Formula VII-5, Formula VIII-1, Formula VIII-2, Formula IX-1, Formula IX-2, Formula X-1, Formula X-2, or a pharmaceutically acceptable salt thereof, or a composition thereof in the treatment of lymphoma. The disclosure features use of a PARP-1 inhibitor according to Formula I, Formula IV-1, Formula IV-2, Formula IV-3, Formula IV-4, Formula V, Formula VI, Formula VII-1, Formula VII-2, Formula VII-3, Formula VII-4, Formula VII-5, Formula VIII-1, Formula VIII-2, Formula IX-1, Formula IX-2, Formula X-1, Formula X-2, or a pharmaceutically acceptable salt thereof, or a composition thereof in the treatment of leukemia. The disclosure features use of a PARP-1 inhibitor according to Formula I, Formula IV-1, Formula IV-2, Formula IV-3, Formula IV-4, Formula V, Formula VI, Formula VII-1, Formula VII-2, Formula VII-3, Formula VII-4, Formula VII-5, Formula VIII-1, Formula VIII-2, Formula IX-1, Formula IX-2, Formula X-1, Formula X-2, or a pharmaceutically acceptable salt thereof, or a composition thereof in the treatment of glioblastoma. Use may be in the manufacture of a medicament for cancer treatment as provided.

The following examples are provided to describe the invention in greater detail. They are intended to illustrate, not to limit, the invention.

EXAMPLE 1

Materials and Methods

Small molecule clustering methods. Inhibitor molecules were imported as SMILES format in the software program Canvas 1.6. Binary hashed fingerprints were calculated from the 2D structure using a dendritic methodology. These generated finger prints were then used as the basis for clustering inhibitors by two methods. The first utilized hierarchical clustering with a Tanimoto similarity metric and Schrödinger cluster linkage method yielded 22 clusters by default. Alteration of the merging distance parameter in the resulting dendrogram from 0.96 to 0.9 yielded 96 clusters. The second clustering methodology involved self-organizing maps calculated according to the sum of fingerprint distances to 27 known PARP inhibitors. Molecules were parsed into a 10 by 10 grid according to this self-organizing approach, measuring similarity to known inhibitors. Twenty seven individual heat maps of the 10 by 10 grid showing distance to individual inhibitors were output for comparison.

Human cell cultures. Human breast carcinoma cell line BT474 [31] was cultured in RPMI 1640 with 10% FBS, sodium pyruvate (10 mM), N-2-hydroxyethylpiperazine-N'-2-ethanesulfonic acid (10 mM) and antibiotics. Androgen-independent human PC-3 prostate cancer cells [32] were obtained from ATCC (Rockville, Md.). Cells were cultured in RPMI 1640 (Bio-Whittaker, Walkersville, Md.) supplemented with 10% FBS (Hyclone, Logan, Utah), penicillin (100 U/ml), streptomycin (100 ug/ml), sodium pyruvate (1 mM) and non-essential amino acids (0.1 mM) under conditions indicated in the figure legends. Normal prostate epithelium cells RWPE-1 were obtained from ATCC (Rockville, Md.). RWPE-1 cells were maintained in Keratinocyte-Serum Free medium (Invitrogen, Carlsbad, Calif.) supplemented with 5 ng/ml of human recombinant EGF and 0.05 mg/ml of bovine pituitary extract. Ovarian cancer cell lines were a kind gift from the Dennis Connolly lab. The NKE cells were obtained from ATCC (Rockville, Md.). The PNX cell line was a gift. Tumor cells were isolated from tumor tissue specimen obtained with written informed consent and Fox Chase Cancer Center Institutional Review Board approval from a patient undergoing tumor resection at the Fox Chase Cancer Center.

PARP-1 inhibitory assay in human cell culture. Different doses of new non-NAD-like PARP-1 inhibitors or classical PARP-1 inhibitors 4ANI and PJ34 were added to the cells cultured in the complete medium. After 24 or 48 hrs, cells were lysed, and protein samples were analyzed with SDS-PAGE and Western Blot using anti-pADPr antibody.

Clonogenic cell survival assay. Cells were plated into 24-well plates at a density of 2000 cells/well. Cells were allowed to adhere overnight at 37° C. and treated with increasing concentrations of non-NAD-like PARP-1 inhibitors or classical PARP-1 inhibitor, Olaparib for 14 days. Colonies were fixed with 70% ethanol for 10 min and stained with 0.25% methylene blue in 30% ethanol for 10 min. After that, staining solution was removed, and plates were rinsed with water. Colonies consisting of 50 cells or more were counted. Plating efficiencies (PE) were calculated as follows: PE=number of colonies/number of cells seeded. The surviving fraction (SF) was calculated as follows: SF=number of colonies/number of cells seeded×PE.

Antibodies. The following antibodies were used: rabbit polyclonal anti-PARP-1 (C2-10, Trevigen), anti-B-Actin (Mouse monoclonal, Sigma, #A5441) and anti-pADPr (Mouse monoclonal, Tulip, #1020). Either goat anti-rabbit or anti-mouse secondary antibodies were conjugated to horseradish peroxidase (Sigma).

Western blotting. For semi-quantitative protein analysis, whole extracts were prepared by boiling cells or homogenized third-instar larvae for 10 min in SDS sample buffer [25 mM Tris (pH 6.8), 2% β-mercaptoethanol, 3% SDS, 0.1% bromophenol blue, 5% glycerol] at 1×10$^7$ cells/ml, and proteins were resolved by SDS-PAGE and transferred to i-Blot (Invitrogen). Detection was performed with ECL-Plus (Amersham) and HyBlot CL Autoradiography Film. Image digitizing and quantitative analysis were performed by Odyssey v1.2 software (LI-COR, Lincoln, Nebr.).

PARP-1 activity assay. 1 μl of H4-histone (1γ/μl) or endonuclease-digested plasmid DNA (0.01 γ/μl) was mixed with 25 μl 200 μM NAD and 1 μl of inhibitor/water. This mixture was combined with 10×PARP-1 reaction buffer (500 mM Tris, pH8.0, 250 mM $MgCl_2$, 1% Triton X-100) and 0.7 μl PARP-1 enzyme (0.1γ/μl, Trevigen). All the reactions were carried out for 30 min at room temperature. Samples were examined with SDS-PAGE and Western Blot using anti-pADPr antibody.

EXAMPLE 2

PARP-1 Inhibitor Screen

Figure 1E:
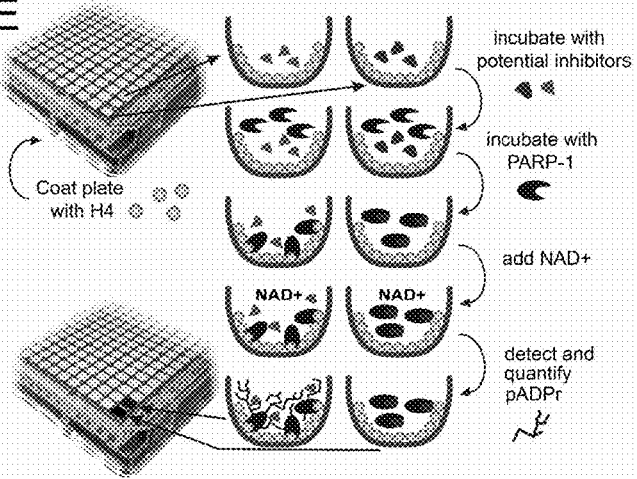

A PARP-1 activation screening assay was designed using a 384-well ELISA plate coated with histone H4 protein-activator. PARP-1 reactions were set up in each well in presence of single a small molecule compound or a positive and a negative control. Compounds that disrupt PARP-1 interaction with H4 activator or compete with NAD+ diminish or abolish accumulation of poly-(ADP)-ribose, the product of these reactions (FIG. 1E). The product of these reactions, poly-(ADP)-ribose, was quantified. Absorbance at 650 or 450 nm was used as an indicator of PARP-1 activity (FIG. 2A). As the test library for this screening assay, the ICCB Known Bioactives library of 480 compounds was used, which includes all popular PARP-1 inhibitors.

Figure 1F:
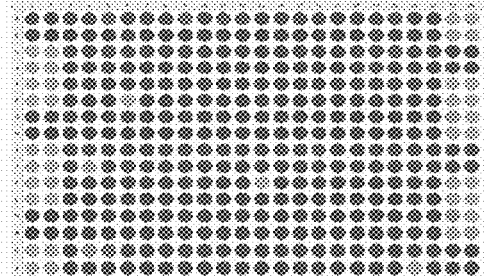
Figure 1G:
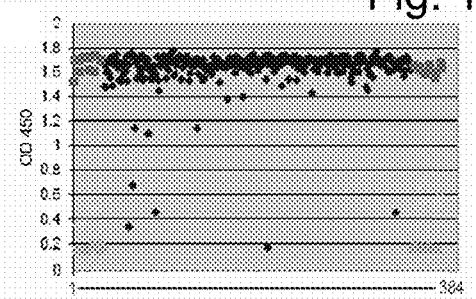
Figure 2E:
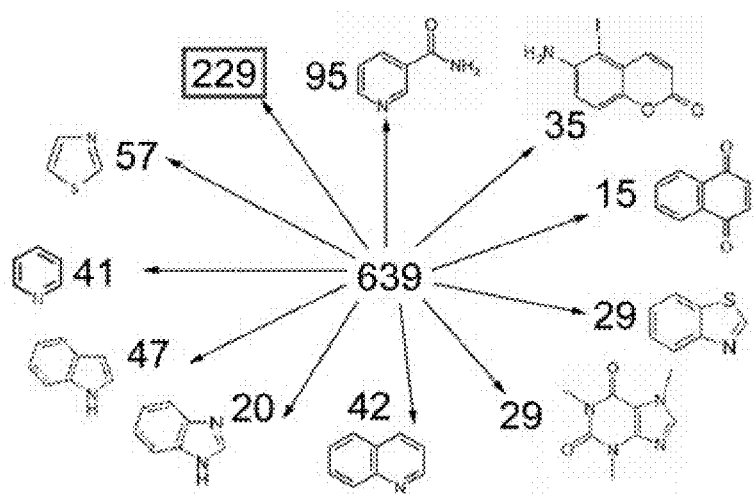

In addition to two known PARP-1 inhibitors, the pilot screening of test library identified twenty three molecules previously unknown as PARP-1 inhibitors (Table 4). Following the pilot screen, analysis of 50,000 small compounds was carried out, and positive hits which reduced PARP-1 activity by at least 3-fold were selected (positive hits which significantly reduced PARP-1 activity in two replicas (FIGS. 1F and 1G)). Nine hundred three small molecules inhibiting PARP-1 were identified in this cell-free system. After eliminating redundancies that display negligible structural differences, 639 of selected compounds were re-analyzed, confirming that all strong positive hits were 100% reproducible. 373 small molecules in this list inhibited PARP-1 at the same or better level than commonly used PARP-1 inhibitors 4-ANI and PJ34. A large number of the newly identified PARP-1 inhibitors demonstrated obvious structural similarities to the known PARP-1 inhibitors. A computation approach was employed to narrow down the list of small molecules for further analysis. First, new PARP-1 inhibitors were sorted based on the presence of an obvious structural core, similar to known biologically active molecules. Nine subgroups were identified based on this approach (FIG. 2E).

TABLE 4

| Value | Position | NAME | |
|---|---|---|---|
| 1.22 | 2-H9 | A-23187 | Calcium ionophore |
| 2.34 | 3-C2 | Loperamide | Calcium channels |
| 2.01 | 3-D6 | PCO-400 | Potassium channels |
| 2.07 | 4-A4 | b-Lapachone | topoisomerase 1 inhibitor |
| 2.06 | 4-A5 | Parthenolide | IkappaB kinase inhibitor |
| 1.89 | 4-A9 | Cycloheximide-N-ethylethanoate | FKBP12 inhibitor |
| 0.05 | 4-B2 | Ebselen | glutathione peroxidase mimetic |
| 1.28 | 4-C7 | AG213 (Tyrphostin 47) | EGF-R tyrosine kinase inhibitor |
| 0.05 | 4-D6 | Amino-1,8-naphthalimide [4-Amino-1,8-naphthalimide] | PARP inhibitor |
| 2.03 | 4-H11 | Cytochalasin B | F actin capper |
| 2.00 | 5-A6 | Decoyinine | lowers GTP levels |
| 2.01 | 5-A9 | Dexamethasone | corticosteroid |
| 0.50 | 5-B3 | 6,7-ADTN HBr | Dopamine agonist |
| 0.20 | 5-B5 | Diphenyleneiodonium Cl | flavoprotein inhibitor |
| 0.05 | 5-D6 | H9 | kinase inhibitor |
| 0.94 | 5-E8 | IBMX | PDE inhibitor (broad spec), adenosineR agonist |
| 0.69 | 6-A9 | PD 98059 | MEK inhibitor |
| 0.05 | 6-B2 | Phenanthridinone [6(5H)-Phenanthridinone] | PARP inhibitor |
| 0.18 | 6-B10 | Propidium iodide | DNA intercalator |
| 0.18 | 6-C5 | Quercetin | kinase inhibitor (plus other) |
| 1.25 | 6-D6 | Indirubin | GSK-3beta inhibitor |
| 1.43 | 6-D11 | Piceatannol | Syk inhibitor |
| 1.90 | 6-H11 | Wiskostatin | N-WASP inhibitor |
| 0.18 | 4-D7 | 3AB | PARP inhibitor |

EXAMPLE 3

N-methylpiperidin/N-methylmorpholino/N-methylpyrrolidine/dipxolanyl Group of New PARP-1 Inhibitors Even without a common structural core molecule, the compounds could expose their epitopes in a similar way to NAD-like PARP-1 inhibitors. The software Canvas 1.6 was used to eliminate small molecules that display even minimal structural similarity to known PARP-1 inhibitors. The information about structure of small molecules was imported in SMILES format. Clustering analysis was used and based on self-organizing maps calculated as the sum of the fingerprint distances to the 27 known PARP-1 inhibitors and NAD (Table 5). Similarity was higher in closely positioned cells and decreased with distance. Molecules distributed in this matrix were compared to each known PARP-1 inhibitor and NAD. The degree of similarity in each cell was represented using heat colors. After super-exposing these maps, an area of the matrix with no similarity to known PARP-1 inhibitors and NAD was identified. This method identified a group of 17 small molecules that show no significant structural similarity to known inhibitors and NAD (Tables 1-3).

Figure 3A:
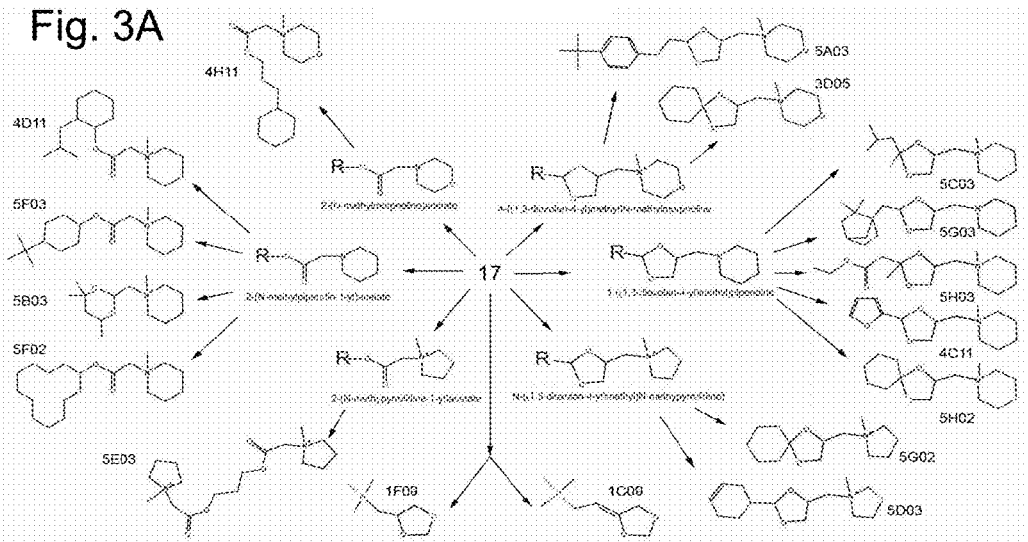
FIGS. 3A through 3F show non-NAD-like PARP-1 inhibitors block PARP-1 activity in human cells.

All of these molecules showed a strong capacity to inhibit PARP-1 in vitro (Tables 1-3). Structurally, these molecules could be split into two subgroups (FIG. 3A): the first, (TABLE 1), contains core element of 2-(N-methylpiperidin-1-yl)acetate or 2-(N-methylmorpholino)acetate or 2-(N-methylpyrrolidine-1-yl)acetate; the second, (TABLE 2), contains core element 1-((1,3-dioxolane-4-yl)methyl)piperidine or 1-((1,3-dioxolane-4-yl)methyl)N-methylmorpholino or 1-((1,3-dioxolane-4-yl)methyl)N-methylpyrrolidine. In addition, two molecules showed similarities to the second group in that they also possess dioxolane-4-yl in their structure (TABLE 3), but are structurally quite distinct in other respects. These new non-NAD-like PARP-1 inhibitors have no obvious structural homologues among components of eukaryotic enzymatic pathways. Therefore, it is believed that they should have greater efficacy and lower side toxicity than classical NAD-like PARP-1 inhibitors. Since inhibiting PARP-1 protein in a cell-free system does not warrant activity of compound in the cell, selected compounds were further tested for their ability to block PARP-1 in human cells.

TABLE 5

| Name | CID* | SMILES |
|---|---|---|
| NAD | 5893 | C1=CC(=C[N+](=C1)C2C(C(C(O2)COP(=O)(O)OP(=O)-(O)CC3C(C(C(O3)N4C=NC5=C4N=CN=C5N)O)O)O)O)C(=O)N |
| Nicotinamide | 936 | C1=CC(=CN=C1)C(=O)N |
| 3AB/PARP inhib. I | 1645 | C1=CC(=CC(=C1)N)C(=O)N |
| PARP Inhibitor II, INH2BP | 72356 | C1=CC(=O)OC2=C1C(=C(C=C2)N)I |
| PARP Inhibitor III, DPQ | 3164 | C1CCN(CC1)CCCCOC2CNC(=O)C3=CC=CC=C23 |
| PARP Inhibitor IV, IQD | 1340 | C1=CC2=C(C=CNC2=O)C(=C1)O |
| 4-ANI/PARP inhib. V | 1720 | C1=CC2=C(C=CC3=C2C(=C1)C(=O)NC3=O)N |
| PARP Inhibitor VI, NU1025 | 63306 | CC1=NC(=O)C2=C(N1)C(=CC=C2)O |
| 6(5H)-Phenanthridinone | 1853 | C1=CC=C2C(=C1)C3=CC=CC=C3NC2=O |
| PARP Inhibitor VIII, PJ34 | 16760621 | CN(C)CC(=O)NC1=CC2=C(C=C1)NC(=O)C3=CC=CC=C32•Cl |
| PARP Inhibitor IX, EB-47 | 16760406 | C1CN(CCN1CC(=O)NC2=CC=CC3=C2CNC3=O)C(=O)-C4C(C(C(O4)N5C=NC6=C5N=CN=C6N)O)O•O•O•Cl•Cl |
| PARP inhibitor X, TIQ-A | 9899130 | C1=CC=C2C(=C1)C3=C(NC2=O)SC=C3 |

TABLE 5-continued

| Name | CID* | SMILES |
|---|---|---|
| PARP Inhibitor XI, DR2313 | 10219702 | CC1=NC(=O)C2=C(N1)CCSC2 |
| PARP Inhibitor XII | 57347661 | CC1=CC=C(C=C1)C2=NC3=C(C=CC=C3N=C2)C(=O)N |
| PARP Inhibitor XV, UPF-1035 | 659976 | C1=CC=C(C=C1)C(=O)OC2=CC=CC3=C2C=CNC3=O |
| Olaparib | 23725625 | C1CC1C(=O)N2CCN(CC2)C(=O)C3=C(C=CC(=C3)CC4=NNC(=O)C5=CC=CC=C54)F |
| ABT-888 (Veliparib) | 11960529 | CC1(CCCN1)C2=NC3=C(C=CC=C3N2)C(=O)N |
| Rucaparib | 9931954 | CNCC1=CC=C(C=C1)C2=C3CCNC(=O)C4=CC(=CC(=C34)N2)F |
| BSI-201 Iniparib | 9796068 | C1=CC(=C(C=C1C(=O)N)[N+](=O)[O-])I |
| AG14361 | 9840076 | CN(C)CC1=CC=C(C=C1)C2=NC3=CC=CC4=C3N2CCNC4=O |
| A-966492 | 16665853 | C1CC(NC1)C2=CC(=C(C=C2)C3=NC4=C(C=CC=C4N3)C(=O)N)F |
| MK-4827 | 24958200 | C1CC(CNC1)C2=CC=C(C=C2)N3C=C4C=CC=C(C4=N3)C(=O)N |
| BYK49187 | 15285131 | CC1=C(N=CN1)C2CCN(CC2)C3=NC4=CC=CC5=C4N3CCC5=O |
| BYK20370 | 25113763 | CC1=C(N2C=C(C=C(C2=N1)O)Cl)C |
| Pyrrolocarbazole derivative (only similar to published inh.) | 58890072 | C1CC2=C(CCC1=O)C3=C(C4C2NC5=CC=CC=C45)C(=O)NC3=O |
| Diminazene | 2354 | C1=CC(=CC=C1C(=N)N)NN=NC2=CC=C(C=C2)C(=N)N |
| Hoechst 33342 | 1464 | CCOC1=CC=C(C=C1)C2=NC3=C(N2)C=C(C=C3)C4=NC5=C(N4)-C=C(C=C5)N6CCN(CC6)C |

*CID, PubChem Compound Identification

EXAMPLE 4

New PARP-1 Inhibitors Block PARP-1 Activity in Cancer Derived Cells

Figure 3B:
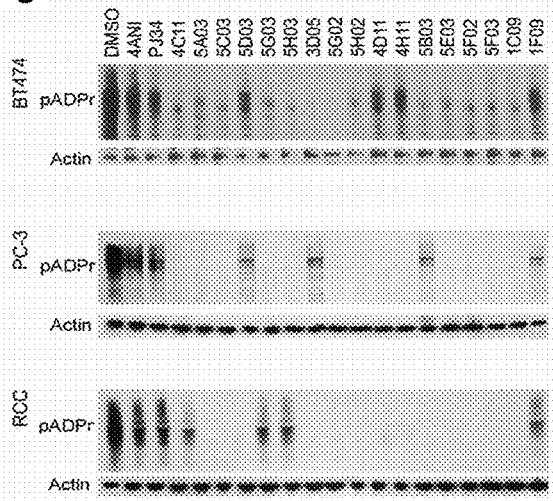

To determine whether the compounds are capable of inhibiting PARP-1 in cells, their action was tested in human cancer-derived cells. Since it was previously determined that breast-(BT474), prostate-(PC3), and kidney (PNX)-cancer derived cells show an unusually high level of PARP-1 activity, BT474 and PC3 cell cultures were used to test the inhibition of PARP-1. Culturing these cells with NAD-competitors, 4ANI or PJ34, diminished pADPr amounts considerably (FIG. 3B). Likewise, all 17 molecules identified by the screen assay of Example 2 showed a similar magnitude of PARP-1 inhibition in human cancer cells (FIG. 3). Therefore, the capacity of these inhibitors to eliminate cancer cells was tested next.

Figure 3C:
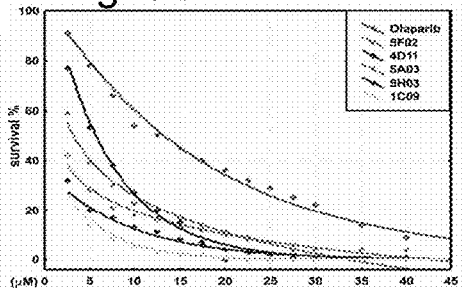
Figure 3D:
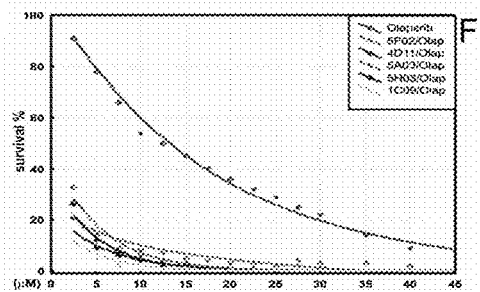
Figure 3E:
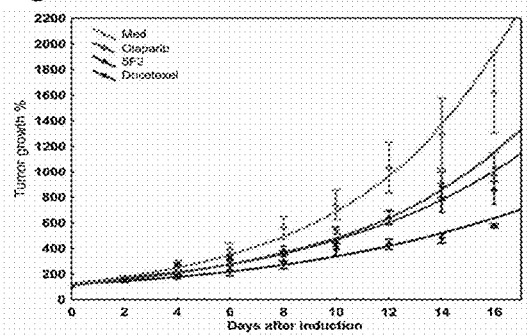
Figure 3F:
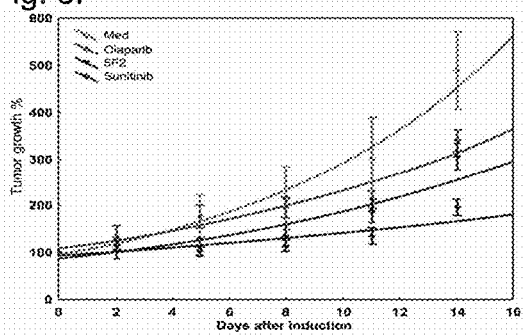

The capacity of new PARP-1 inhibitors to specifically suppress the tumorigenic potential of human cancer-derived cells was tested. The capacity of these molecules to suppress the clonogenic growth of prostate cancer PC-3 cells was compared. Unlike normal cells, cancer derived cells are capable of establishing colonies growing on agar plates. The action of Olaparib was compared with five new non-NAD-like inhibitors (5F02, 4D11, 5A03, 5H03, 1C09) separately and as dual therapy with Olaparib. Although, effects of each individual new compound on PC-3 cells growth varied considerably, all of them suppressed growth of the colonies with greater efficacy than classical Olaparib (FIG. 3C). Moreover, non-NAD-like inhibitors synergistically enhance the effect of NAD-competitors on the suppression of colonies' growth (FIG. 3D).

In light of encouraging in vitro data, the antitumor activity of non-NAD-like inhibitor 5F2 was examined using an androgen-independent PC-3 prostate cancer and renal cell carcinoma (RCC) xenograft animal models. As demonstrated in FIGS. 3E and F, animals treated with non-NAD-like inhibitor 5F02 showed a significantly stronger inhibition of tumor growth relative to control animals and animals treated with the classical Olaparib or clinically approved anti-cancer drugs, docetaxel for prostate and Sunitinib for kidney cancer. Importantly, treatment with 5F02 was well tolerated by all animals, with no apparent signs of toxicity.

EXAMPLE 5

SUMMARY

Clinical interest in PARP-1 skyrocketed over the past decade with the recognition of its roles in transcription regulation, DNA repair, epigenetic bookmarking, and chromatin restructuring. Currently, there are over one hundred clinical studies evaluating PARP-1 inhibitors; the overwhelming majority of which are in oncology. Given the initial promising results for treating certain types of cancer, there is a need for more effective and less cytotoxic PARP-1 inhibitors.

Whereas the NAD-dependent route of PARP-1 activation have been exhaustively exploited for designing new inhibitors, the other two known routes of its activation, the histone H4-dependent and DNA-dependent pathways, remain overlooked. These data show the discovery of new PARP-1 inhibitors using a screen based on PARP-1 enzymatic activation via histone H4. Although the screening for compounds inhibiting H4-induced PARP-1 activity also identified molecules similar in structure to NAD, including those acting similarly to previously known PARP-1 inhibitors, other inhibitors identified by the screen represent a new generation of PARP-1 inhibitors that are not NAD analogues. Because NAD is a crucial metabolic currency within cells, compounds that mimic NAD disrupt multiple cellular processes, leading to off target effects. Therefore, the new non-NAD-like inhibitors are significantly less cytotoxic than previously known conventional inhibitors.

The new non-NAD-like PARP-1 inhibitors demonstrate higher efficacy against several types of tumors than the classical NAD-like PARP-1 inhibitors. Activation of PARP-1 via histone H4 has been best described within the context of transcription regulation and changes in chromatin structure. The expanse of histone mediated PARP-1 activity, however, within the various known functions of PARP-1 (e.g., DNA repair) is yet to be fully understood. The mechanism of action of these new generation PARP-1 inhibitors is not clear and may involve several routes, e.g., obstruction of PARP-1 interaction with H4 or provoking an inhibitory conformational change.

When PARP-1 inhibitors were first evaluated for their potential in treating cancer, the underlying rationale for their application was to prevent PARP-1 mediated DNA repair, thereby reducing survival potential of carcinogenic cells. Consequently, in oncology, PARP-1 inhibitors have been primarily tested either to increase the efficacy of cytotoxic therapies or as a monotherapy via synthetic lethality in tumors with already notable defective DNA repair pathways, namely homologous recombination. The synthetic lethality approach has been most extensively explored in BRCA1/2-deficient ovarian and breast cancers.

Although the first PARP-1 inhibitor was recently approved by the FDA for treatment of ovarian cancer in women with BRCA1/2 mutations whom have already failed three or more chemotherapy treatments, there have been drastically varied responses in patients with BRCA mutations and even improved outcomes in cohorts of patients with wild-type BRCA genes. It has been speculated that PARP-1 inhibitor efficacy in oncology extends into its role in regulating transcription and chromatin structure. Maintaining an active chromatin state for transcribing genes is the central component in rapidly dividing cells, particularly those that are carcinogenic. It has also been shown that PARP-1 plays an integral role in transcription regulation of hormone-dependent cancers. It is believed that the role of PARP-1 inhibitors in oncology extends beyond the initial excitements targeting the role of PARPs in DNA repair.

Apart from oncology, preclinical efficacy of PARP-1 inhibitors in mitigating inflammation, circulatory shock, myocardial infarction, and stroke is likely due to the inhibition of PARP-1 transcription regulation. So far, the introduction of these inhibitors beyond oncology has been hampered by the possible risks of toxicity and carcinogenesis, secondary to inhibiting an integral component of DNA repair. However, the extent of PARP-1 mediated transcription in DNA repair is not entirely clear.

EXAMPLE 6

Selectivity of New PARP-1 Inhibitors for Eliminating Cancer-Derived Cells

Figure 4:
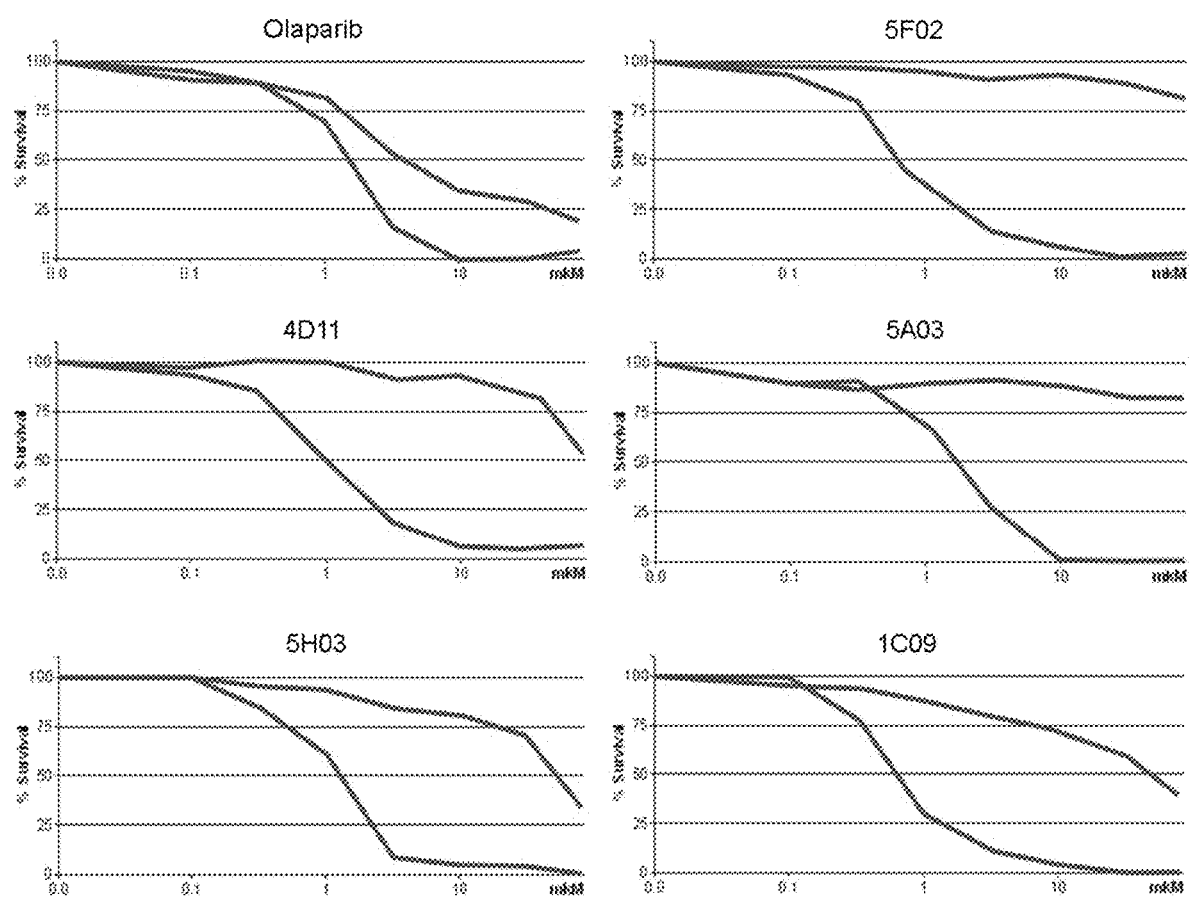
FIG. 4 shows cell survival assays. Normal cells and cancer-derived cells were plated at a density of 104 cells/well (100 µl) in a 96-well plate. On the next day, Olaparib, a NAD-mimetic, or 5F02, 4D11, 5A03, 5H03, 1C09, new non-NAD-like inhibitors, were added. Cells were grown for 72 hr. 20 µl/well of alamarBlue® reagent was added; fluorescence readings were taken. New inhibitors eliminated cancer cells with low cytotoxicity to normal cells, while Olaparib killed both normal and cancer cells.

The cytotoxic effects of treatment by classical inhibitor Olaparib and the new inhibitors was compared using breast cancer-derived cells BT474 and normal breast-derived cells HMEK. It was observed that, although both Olaparib and the inhibitors eliminate cancer-derived cells at similar concentrations, the new inhibitors showed significantly lower cytotoxicity to normal cells (FIG. 4).

EXAMPLE 7

New Inhibitors Suppress Tumorigenic Potential of Cancer Derived Cells

Figure 5:
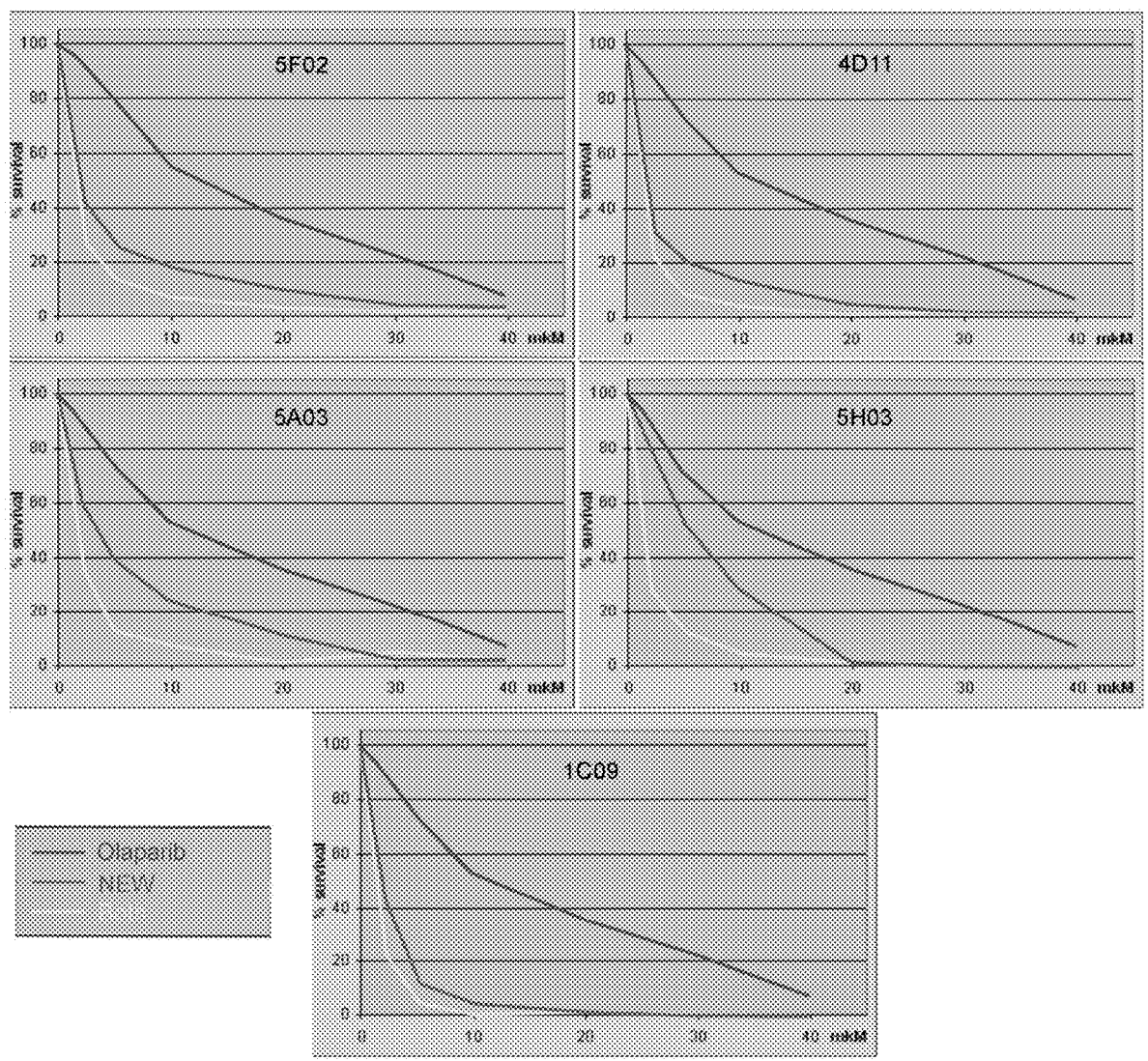
FIG. 5 shows that the new PARP-1 inhibitors suppress malignancy potential of PC-3 cells. Clonogenic cell survival assays: PC-3 cells were plated into 24-well plates. Cells were allowed to adhere overnight and were treated with one of non-NAD-like inhibitor (5F02, 4D11, 5A03, 5H03, 1C09) (blue), Olaparib (magenta), and both (yellow) for 14 days. Colonies were counted and plotted on the graph.

The capacity of new PARP-1 inhibitors to specifically suppress the tumorigenic potential of human cancer-derived cells was tested. The capacity of these molecules to suppress the clonogenic growth of prostate cancer PC-3 cells was also tested. Unlike normal cells, cancer derived cells are capable of establishing colonies growing on agar plates. The action of Olaparib was compared to five new non-NAD-like inhibitors (5F02, 4D11, 5A03, 5H03, 1C09) separately and together. Although effects of each individual new compound on PC-3 cells growth varied considerably, all of them suppressed colony growth with greater efficacy than Olaparib (FIG. 5).

EXAMPLE 8

Figure 6A:
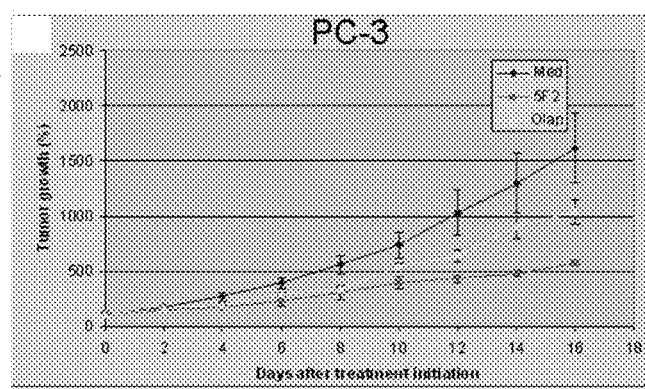
FIGS. 6A through 6C show non-NAD-like PARP-1 inhibitors suppress tumor growth in vivo. 5F02 inhibitor suppresses growth of androgen-independent PC-3 (FIG. 6A) and renal cell carcinoma (PNX) (FIG. 6B) xenograft tumors in vivo. Ectopic PC-3 or RCC xenograft tumors were established in 6-week-old male C.B17/Icr-scid mice. Animals were treated intraperitoneally with non-NAD-like inhibitor 5F02 (23 mg/kg), classical PARP-1 inhibitor Olaparib (Olap) (50 mg/kg) or vehicle (PBS) 5 days a week. Values shown represent means (n=5)+SEM.
Figure 6B:
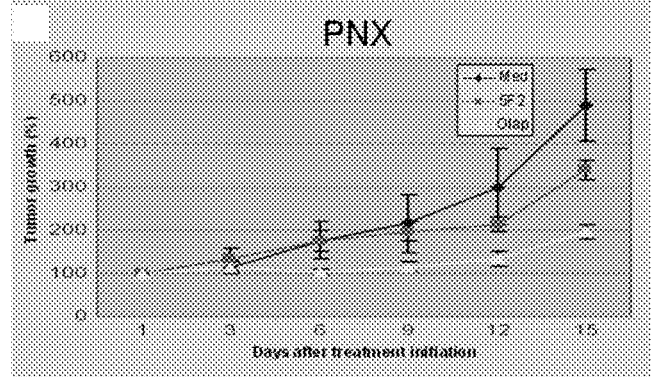
Figure 6C:
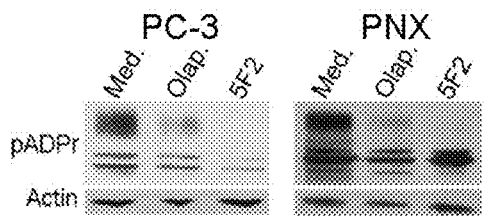

New PARP-1 Inhibitors Suppress Growth of Patient-Derived Xenograft Tumors In Vivo In light of encouraging in vitro data, the antitumor activity of non-NAD-like inhibitor 5F02 was further tested using an androgen-independent PC-3 prostate cancer and renal cell carcinoma (RCC) xenograft in animal models. As demonstrated in FIG. 6, animals treated with non-NAD-like inhibitor 5F02 showed a significantly stronger inhibition of tumor growth relative to control animals and animals treated with the classical Olaparib. Importantly, treatment with 5F02 was well tolerated by all animals, with no apparent signs of toxicity.

The invention is not limited to the embodiments described and exemplified above, but is capable of variation and modification within the scope of the appended claims.

I claim:

1. A compound of Formula

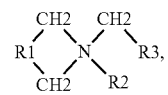

wherein:
R1 is an alkyl or ether group;
R2 is CH$_3$, wherein the nitrogen atom is positively charged, and
R3 is either

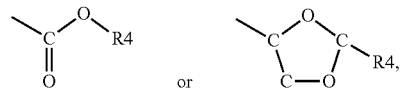

wherein R4 is cyclohexane, cyclohexene, substituted phenyl, pyrrolidine, or norbornane.

2. The compound of claim 1, wherein R3 is:

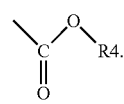

3. The compound of claim 2, wherein the R1 is —(CH$_2$)$_3$—.

4. The compound of claim 1, wherein the compound is:

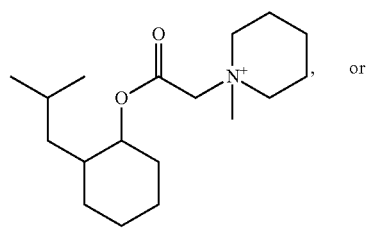, or

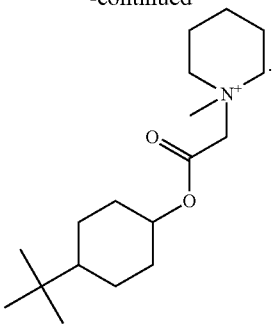

5. The compound of claim 2, wherein R1 is (CH$_2$)O(CH$_2$)—.

6. The compound of claim 5, wherein the compound is:

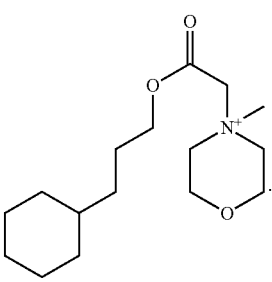 [SMILES: C[N+]1(CC(=O)OCCCC2CCCCC2)CCOCC1]

7. The compound of claim 2, wherein R1 is —(CH$_2$)$_2$—.

8. The compound of claim 7, wherein the compound is:

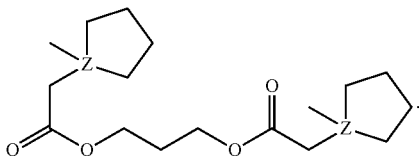

9. The compound of claim 1, wherein R3 is:

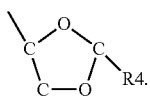

10. The compound of claim 9, wherein R1 is —(CH$_2$)$_3$—.

11. The compound of claim 10, wherein the compound is:

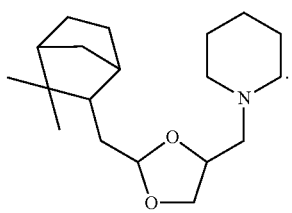 [SMILES: CC1(C)C2CCC(C2)C1CC1OCC(CN2CCCCC2)O1]

12. The compound of claim 9, wherein R1 is —(CH$_2$)O(CH$_2$)—.

13. The compound of claim 12, wherein the compound is:

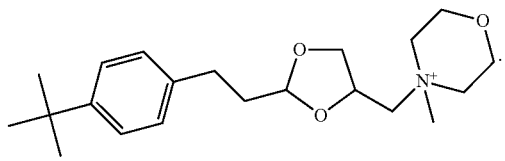 [SMILES: CC(C)(C)c1ccc(CCC2OCC(C[N+]3(C)CCOCC3)O2)cc1]

14. The compound of claim 9, wherein R1 is —(CH$_2$)$_2$—.

15. The compound of claim 14, wherein the compound is:

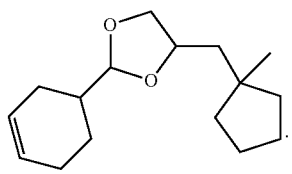 [SMILES: CC1(CC2COC(C3CC=CCC3)O2)CCCC1]

16. A compound which is

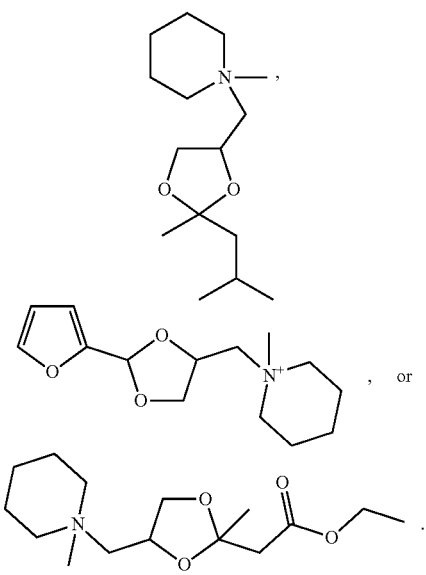

17. A composition, comprising the compound of claim 1 and a carrier.

18. The composition of claim 17, wherein the carrier is a pharmaceutically acceptable carrier.

19. A method for inhibiting the biologic activity of poly(ADP-ribose) polymerase 1 (PARP1), comprising contacting PARP1 with an amount of a compound effective to inhibit the biologic activity of PARP1, the compound comprising:

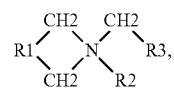

wherein:
R1 is an alkyl or ether group;
R2 is CH$_3$, wherein the nitrogen atom is positively charged, and
R3 is either

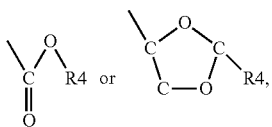

wherein R4 is cyclohexane, cyclohexene, substituted phenyl, pyrrolidine, or norbornane.

20. A method for inhibiting the biologic activity of poly(ADP-ribose) polymerase 1 (PARP1), comprising contacting PARP1 with an amount of a compound effective to inhibit the biologic activity of PARP1, wherein the compound is:

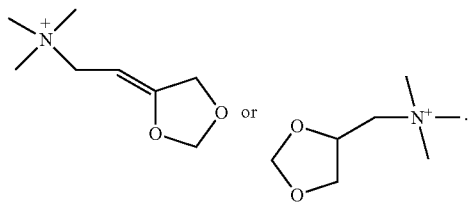

21. A method for treating a patient having prostate cancer, breast cancer, or kidney cancer, comprising administering to the patient in need thereof an effective amount of the compound of Formula

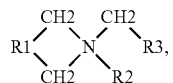

wherein:
R1 is an alkyl or ether group;
R2 is either $CH_3$ or not present, wherein when R2 is $CH_3$, the nitrogen atom is positively charged, and
R3 is either

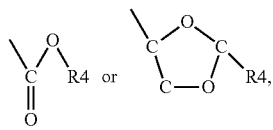

wherein R4 is cyclohexane, cyclohexene, substituted phenyl, pyrrolidine, or norbornane, thereby treating the cancer in the patient.

22. The method of claim 21 wherein: the cancer patient is a prostate cancer patient and the cancer is prostate cancer.

* * * * *

UNITED STATES PATENT AND TRADEMARK OFFICE
CERTIFICATE OF CORRECTION

| | |
|---|---|
| PATENT NO. | : 10,550,108 B2 |
| APPLICATION NO. | : 15/515773 |
| DATED | : February 4, 2020 |
| INVENTOR(S) | : Alexei Tulin |

It is certified that error appears in the above-identified patent and that said Letters Patent is hereby corrected as shown below:

In the Specification

In the STATEMENT OF GOVERNMENT SUPPORT Section on Column 1, Lines 17-20, delete the existing paragraph "The inventions described herein were made, in part, with funds obtained from the National Institutes of Health, Grant Nos. R01 GM077452 and R01 DK082623. The U.S. government may have certain rights in these inventions." and insert therefore -- This invention was made with government support under GM077452, and DK082623 awarded by the National Institutes of Health. The government has certain rights in the invention. --

Signed and Sealed this
Fifth Day of September, 2023

Katherine Kelly Vidal
*Director of the United States Patent and Trademark Office*